US009744163B2

(12) United States Patent
Ottoboni et al.

(10) Patent No.: US 9,744,163 B2
(45) Date of Patent: *Aug. 29, 2017

(54) COMPOSITIONS OF A POLYORTHOESTER AND AN APROTIC SOLVENT

(71) Applicant: Heron Therapeutics, Inc., Redwood City, CA (US)

(72) Inventors: Thomas B. Ottoboni, Belmont, CA (US); Lee Ann Lynn Schillinger, San Bruno, CA (US); Joseph Niemann, Fremont, CA (US)

(73) Assignee: Heron Therapeutics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/210,263

(22) Filed: Mar. 13, 2014

(65) Prior Publication Data

US 2014/0275046 A1 Sep. 18, 2014

Related U.S. Application Data

(60) Provisional application No. 61/789,469, filed on Mar. 15, 2013, provisional application No. 61/902,018, filed on Nov. 8, 2013.

(51) Int. Cl.
| | |
|---|---|
| *A61K 9/00* | (2006.01) |
| *A61K 31/4458* | (2006.01) |
| *A61K 47/22* | (2006.01) |
| *A61K 31/439* | (2006.01) |
| *A61K 31/445* | (2006.01) |
| *A61K 31/485* | (2006.01) |
| *A61K 47/20* | (2006.01) |
| *A61K 47/34* | (2017.01) |
| *A61K 47/14* | (2017.01) |
| *A61K 47/18* | (2017.01) |

(52) U.S. Cl.
CPC ........ *A61K 31/4458* (2013.01); *A61K 9/0024* (2013.01); *A61K 31/439* (2013.01); *A61K 31/445* (2013.01); *A61K 31/485* (2013.01); *A61K 47/14* (2013.01); *A61K 47/18* (2013.01); *A61K 47/20* (2013.01); *A61K 47/22* (2013.01); *A61K 47/34* (2013.01)

(58) Field of Classification Search
CPC .............. A61K 31/4458; A61K 31/445; A61K 31/485; A61K 31/439; A61K 9/0024; A61K 47/18; A61K 47/14; A61K 47/34; A61K 47/22; A61K 47/20
USPC ...................... 514/282, 330, 226.5, 279, 299
See application file for complete search history.

(56) References Cited

U.S. PATENT DOCUMENTS

| | | |
|---|---|---|
| 4,079,038 A | 3/1978 | Choi et al. |
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,304,767 A | 12/1981 | Heller et al. |
| 4,946,931 A | 8/1990 | Heller et al. |
| 4,957,998 A | 9/1990 | Heller et al. |
| 5,747,058 A | 5/1998 | Tipton et al. |
| 5,968,543 A | 10/1999 | Heller et al. |
| 6,331,311 B1 | 12/2001 | Brodbeck et al. |
| 6,524,606 B1 | 2/2003 | Ng et al. |
| 6,613,335 B1 | 9/2003 | Ruelle |
| 6,673,767 B1 | 1/2004 | Brodbeck et al. |
| 7,053,209 B1 | 5/2006 | Gibson et al. |
| 8,187,640 B2 | 5/2012 | Dunn |
| 8,206,735 B2 | 6/2012 | Li et al. |
| 8,252,304 B2 | 8/2012 | Ng et al. |
| 2002/0141966 A1 | 10/2002 | Dang |
| 2004/0109893 A1 | 6/2004 | Chen et al. |
| 2005/0042194 A1 | 2/2005 | Ng et al. |
| 2006/0155101 A1 | 7/2006 | Heller et al. |
| 2007/0264338 A1* | 11/2007 | Shah ................... A61K 9/0014 424/484 |
| 2007/0265329 A1 | 11/2007 | Devang et al. |
| 2009/0162301 A1 | 6/2009 | Tarrand |
| 2009/0202436 A1 | 8/2009 | Hobot et al. |
| 2011/0275516 A1 | 11/2011 | Wu et al. |

(Continued)

FOREIGN PATENT DOCUMENTS

| | | | |
|---|---|---|---|
| GB | 2481018 A | * 12/2011 | |
| GB | 2481018 A | * 12/2011 | ........... A61K 9/0024 |

(Continued)

OTHER PUBLICATIONS

Heller et al., "Development of poly(ortho esters) and their application for bovine serum albumin and bupivacaine delivery", J. Contr. Rel., vol. 78, No. 1-3, pp. 133-141 (2002).
International Search Report from PCT Patent Application No. PCT/US2014/026575 mailed May 28, 2014.
Merkli et al., "Purity and stability assessment of a semi-solid poly(ortho ester) used in drug delivery systems", Biomaterials, vol. 17, No. 9, pp. 897-902 (1996).
Dissolution Apparatus Classifications, Stage 6 Harmonization, The United States Pharmacopeial Convention, No. 711, pp. 1-8 (2011).
Michigan State University, "Aprotic Solvents", Online article retrieved from http://www.cem.msu.edu/~reusch/OrgPage/solvent.htm, 3 pages, retrieved Feb. 4, 2015.

*Primary Examiner* — Jason Sims
*Assistant Examiner* — Ibrahim D Bori
(74) *Attorney, Agent, or Firm* — Judy Mohr; McDermott Will & Emery LLP

(57) ABSTRACT

Delivery systems and compositions comprised of a biodegradable polyorthoester polymer, an aprotic solvent, and a drug are described. The solvent is selected to modulate release of drug from the composition, where, in some embodiments, the solvent is rapidly released after administration and provides a corresponding rapid rate of drug release. Alternatively, in other embodiments, the solvent is slowly released from the composition after its administration, and provides a correspondingly slow rate of drug release.

21 Claims, 10 Drawing Sheets

(56) References Cited

U.S. PATENT DOCUMENTS

2014/0275046 A1 9/2014 Ottoboni et al.
2014/0275145 A1 9/2014 Ottoboni et al.
2014/0296282 A1 10/2014 Ottoboni et al.

FOREIGN PATENT DOCUMENTS

| WO | WO 01/85139 A2 | 11/2001 |
| WO | WO 2004/043432 A2 | 5/2004 |
| WO | WO 2004/052336 A2 | 6/2004 |
| WO | WO 2006/033948 A2 | 3/2006 |
| WO | WO 2006/037116 A2 | 4/2006 |
| WO | WO 2007/133752 A2 | 11/2007 |
| WO | WO 2009/129509 A2 | 10/2009 |
| WO | WO 2011/154724 A2 | 12/2011 |
| WO | WO 2014/143635 | 9/2014 |

* cited by examiner

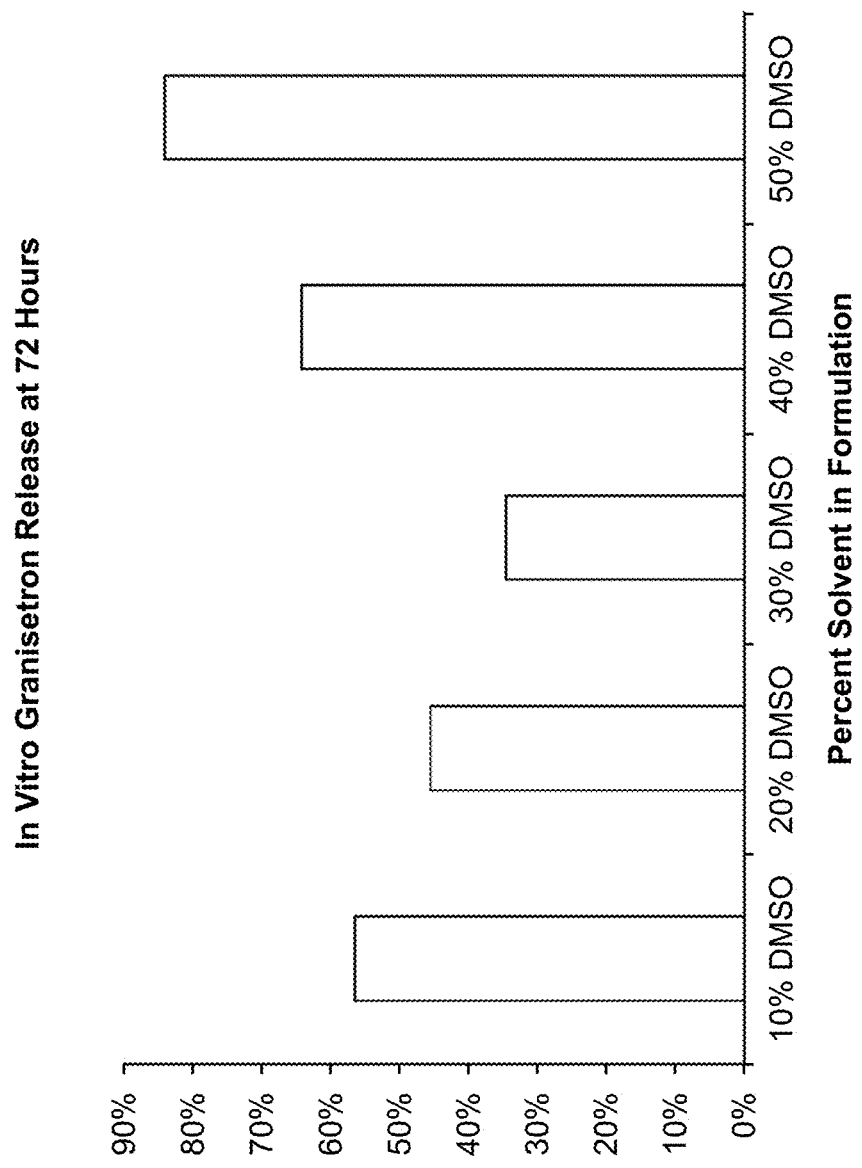

COMPOSITIONS OF A POLYORTHOESTER AND AN APROTIC SOLVENT

CROSS-REFERENCE TO RELATED APPLICATIONS

This application claims the benefit of priority of U.S. Provisional Patent Application No. 61/789,469 filed Mar. 15, 2013, and of U.S. Provisional Patent Application No. 61/902,018 filed Nov. 8, 2013, the contents of which are incorporated herein by reference.

TECHNICAL FIELD

The present disclosure is directed to compositions, systems and methods comprised of a biodegradable polyorthoester polymer, an aprotic solvent, and a drug.

BACKGROUND

Polymer-based depot systems for administering an active agent are well known. These systems incorporate the active agent into a carrier composition, such as a polymeric matrix, from which the active agent is delivered upon administration of the composition to a patient.

Many factors influence the design and performance of such systems, such as the physical/chemical properties of the drug, the physical/chemical characteristics of the system's components and the performance/behavior relative to other system components once combined, as well as external/environmental conditions at the site of application. In designing polymer-based systems for delivery of a drug, the desired rate of drug delivery and onset, the drug delivery profile, and the intended duration of delivery all must be considered.

There remains a need for polymer-based compositions that offer the flexibility to modulate or tailor the rate of drug release. The present systems, compositions, and related methods satisfy this need.

BRIEF SUMMARY

In one aspect, i.e., a first aspect, a delivery system comprised of a polyorthoester, an aprotic solvent in which the polyorthoester is miscible to form a single phase; and a therapeutically active agent dispersed or solubilized in the single phase is provided. The active agent is released from the system over a period of between approximately 1 day and approximately 8 weeks.

In one embodiment, related to any one or more of the aspects or other embodiments provided herein, the delivery system has a viscosity of less than about 10,000 cP at 37° C.

In another embodiment, the solvent is an organic solvent having a water solubility of greater than 25% by weight of the solvent in water at room temperature.

In yet another embodiment, the solvent is a dipolar aprotic solvent.

In still another embodiment, the solvent is in a class selected from the group consisting of an amide, a biocompatible oil, an ester of an acid, an ester of an alcohol, an ether, a ketone, a sulfoxide, a triglyceride, and an ester of a triglyceride.

In one embodiment, the solvent is an amide selected from the group consisting of 2-pyrrolidone, dimethyl formamide, N-methyl-2-pyrrolidone, N-ethyl-2-pyrrolidone, dimethyl acetamide, n-cyclohexyl-2-pyrrolidone and caprolactam.

In another embodiment, the solvent is a biocompatible oil, excluding non-hydrogenated vegetable oils, partially-hydrogenated vegetable oils, peanut oil, sesame oil or sunflower oil.

In still another embodiment, the solvent is an ester of an acid selected from the group consisting of carboxylic acid esters and fatty acid esters, excluding propylene glycol dicaprate and propylene glycol dicaprylate.

In yet another embodiment, the solvent is selected from the group consisting of ethyl acetate, benzyl benzoate, methyl acetate, isopropyl myristate, ethyl oleate, methyl lactate and ethyl lactate.

In another embodiment, the solvent is an ester of an alcohol, and is propylene carbonate (4-methyl-1,3-diololan-2-one).

In one embodiment, the solvent is an ether selected from dimethyl isosorbide and tetrahydrofuran.

In another embodiment, the solvent is a ketone selected from the group consisting of acetone and methyl ethyl ketone.

In still another embodiment, the solvent is a lactone selected from the group consisting of caprolactone and butyrolactone.

In yet another embodiment, the solvent is a sulfoxide selected from the group consisting of dimethyl sulfoxide and decylmethylsulfoxide.

In one embodiment, the solvent is 1-dodecylazacycloheptan-2-one.

In another embodiment, the solvent is not propylene glycol dicaprate, propylene glycol dicaprylate, glycofurol, a non- or partially-hydrogenated vegetable oil, glyceryl caprylate, glyceryl caprate, glyceryl caprylate/caprate, glyceryl 10 caprylate/caprate/laurate, poly(ethylene glycol-copolypropylene glycol, poly(ethylene glycol)monomethyl ether 550, poly(ethylene glycol)dimethyl ether 250, glycerine triacetate, or a triglyceride.

In one embodiment, the therapeutically active agent is an anti-emetic.

In another embodiment, the therapeutically active agent is an anesthetic.

In a further embodiment, the therapeutically active agent is a semi-synthetic opioid.

In another embodiment, the polyorthoester is selected from the polyorthoesters represented by Formulas I, II, III and IV set forth herein below.

In yet a further embodiment, the polyorthoester is represented by Formula III as set forth herein.

In one embodiment, the polyorthoester is represented by the structure shown as Formula III, the active agent is granisetron in an amount between 1-5 percent by weight of the delivery system, and the solvent is DMSO in an amount between 10-35 percent by weight of the delivery system.

In yet another embodiment, the polyorthoester is represented by the structure shown as Formula III in accordance with any one or more of the combinations and sets of variables related thereto as provided herein; the active agent is ropivacaine or bupivacaine in an amount between 3 and 30 percent by weight of the delivery system, and the solvent is selected from dimethyl sulfoxide, dimethyl acetamide and N-methylpyrrolidone in an amount between 15-50 percent by weight of the delivery system.

In another or second aspect, a flowable composition comprised of a polyorthoester, a solvent in which the polyorthoester is miscible to form a single phase; and a therapeutically active agent dispersed or solubilized in the single phase, wherein the solvent is an aprotic solvent with a dipole moment greater than about 2 Debye (D), is provided.

In one embodiment, the solvent is an ester of an alcohol, propylene carbonate (4-methyl-1,3-diololan-2-one).

In another embodiment, the solvent is a ketone selected from the group consisting of acetone and methyl ethyl ketone.

In yet another embodiment, the solvent an amide selected from the group consisting of 2-pyrrolidone, dimethyl formamide, N-methyl-2-pyrrolidone, and dimethyl acetamide.

In still another embodiment, the solvent is a sulfoxide selected from the group consisting of dimethyl sulfoxide and decylmethylsulfoxide.

In one embodiment, the solvent is an ether selected from dimethyl isosorbide and tetrahydrofuran.

In one embodiment, the solvent is a lactone selected from the group consisting of ester-caprolactone and butyrolactone.

The composition, in any embodiment, can comprise as the therapeutically active agent an anti-emetic.

Alternatively, in any embodiment, the composition can comprise as the therapeutically active agent an anesthetic, such as, e.g., ropivacaine or bupivacaine.

Further, the composition, in any embodiment, can comprise as the therapeutically active agent, an opioid such as buprenorphine.

The composition, in any embodiment, can comprise as the polyorthoester a polyorthoester selected from the group represented by Formulas I, II, III and IV set forth herein below.

The composition, in any embodiment, can comprise a viscosity of less than about 10,000 cP at 37° C.

In one embodiment, the polyorthoester is represented by the structure shown as Formula III, the active agent is granisetron in an amount between 1-5 percent by weight of the composition, and the solvent is DMSO in an amount between 10-35 percent by weight of the composition.

In another aspect, a method of administering a therapeutically active agent is provided. The method comprises dispensing from a needle a delivery system or a composition as described herein.

In another aspect, provided is a method of treatment comprising dispensing from a needle a composition comprised of a polyorthoester, an aprotic solvent in which the polyorthoester is miscible to form a single phase; and a therapeutically active agent dispersed or solubilized in the single phase; wherein the solvent is selected to achieve a controlled release of the active agent from the composition according to a predetermined release profile, and wherein the release of the active agent is for a period of between approximately 1 day and approximately 8 weeks.

In one embodiment, the solvent is selected to have a dipole moment greater than about 2 Debye (D).

In another embodiment, the composition has a viscosity of less than about 10,000 cP at 37° C.

Additional embodiments of the present systems, compositions and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE FIGURES

FIGS. 3B-3C are bar graphs showing the percent of active agent, granisetron, released after 24 hours (FIG. 3B) and 72 hours (FIG. 3C) in an in vitro dissolution release test, from compositions comprised of a polyorthoester and varying percentages, 10%, 20%, 30%, 40% or 50% of an aprotic solvent, dimethylsulfoxide (DMSO);

DETAILED DESCRIPTION

I. Definitions

Figure 1A:
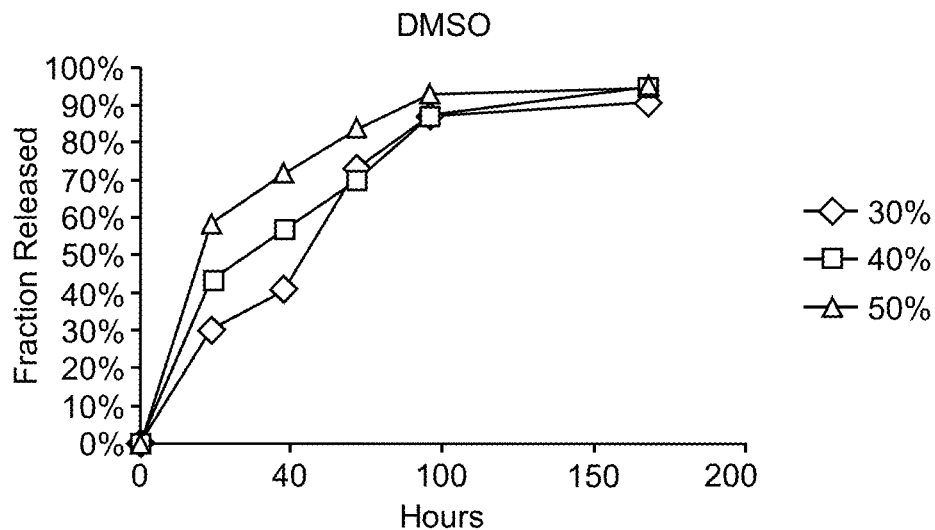
FIGS. 1A-1B are graphs of the percent of solvent released as a function of time, in hours, from a delivery system comprised of a polyorthoester and an aprotic solvent, dimethylsulfoxide (DMSO, FIG. 1A) or dimethyl acetamide (DMAC, FIG. 1B), in an in vitro dissolution apparatus, where in FIG. 1A the compositions comprised 30% DMSO (diamonds), 40% DMSO (squares) and 50% DMSO (triangles), and in FIG. 1B the compositions comprised 20% DMAC (diamonds), 30% DMAC (squares), 40% DMAC (triangles), or 50% DMAC (x symbols)

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

"Molecular mass" in the context of a polymer such as a polyorthoester, refers to the nominal average molecular mass of a polymer, typically determined by size exclusion chromatography, light scattering techniques, or velocity. Molecular weight can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatographic or other liquid chromatographic techniques. Other methods for measuring molecular weight values can also be used, such as the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. It should be noted that certain properties of polymers, e.g., a polyorthoester, such as molecular weight, molecular number, number of monomer subunits (typically indicated by the subscript below brackets enclosing a monomeric subunit of the polymer), and the like, are generally described herein in terms of discrete values, however it will be understood by those of skill in the art that. because of the complex nature of polymers, such values generally refer to average values.

"Bioerodible", "bioerodibility" and "biodegradable", which are used interchangeably herein, refer to the degradation, disassembly or digestion of a polymer by action of a biological environment, including the action of living organisms and most notably at physiological pH and temperature. As an example, a principal mechanism for bioerosion of a polyorthoester is hydrolysis of linkages between and within the units of the polyorthoester.

As used herein, the term "emesis" includes nausea and vomiting.

Solubility values of solvent in water are considered to be determined at 20° C.

A "polymer susceptible to hydrolysis" such as a polyorthoester polymer refers to a polymer that is capable of degradation, disassembly or digestion through reaction with water molecules. Such a polymer contains hydrolyzable groups in the polymer. Examples of polymers susceptible to hydrolysis may include, but is not limited to, polymers described herein, and those described in U.S. Pat. Nos. 4,079,038, 4,093,709, 4,131,648, 4,138,344, 4,180,646, 4,304,767, 4,957,998, 4,946,931, 5,968,543, 6,613,335, and 8,252,304, and U.S. Patent Publication No. 2007/0265329, which are incorporated by reference in their entirety.

"Pharmaceutically acceptable salt" denotes a salt form of a drug having at least one group suitable for salt formation that causes no significant adverse toxicological effects to the patient. Reference to an active agent as provided herein is meant to encompass its pharmaceutically acceptable salts, as well as solvates and hydrates thereof. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate and phosphate. Suitably pharmaceutically acceptable salt forms are found in, e.g., Handbook of Pharmaceutical Salts: Properties, Selection and Use, Weinheim/Zürich:Wiley-VCH/VHCA, 2002; P. H. Stahl and C. G. Wermuth, Eds.

"Polyorthoester-compatible" refers to, in one particular aspect of the properties of the polyorthoester, the properties of an additive or component or solvent which, when mixed with the polyorthoester, forms a single phase and does not cause any physical or chemical changes to the polyorthoester.

A "therapeutically effective amount" means the amount that, when administered to an animal for treating a disease, is sufficient to effect treatment for that disease.

"Treating" or "treatment" of a disease or condition includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e. to a degree of 85% or greater) in reference to the feature or entity.

The term "about", particularly in reference to a given quantity, is meant to encompass deviations of plus or minus five percent.

II. Delivery System and Composition

The systems and compositions described herein comprise a biodegradable polyorthoester polymer combined with a biocompatible organic solvent, and find use, for example, as drug delivery systems or as medical or surgical devices. As will be described herein, the selection of solvent or solvents in the system may be used to modulate the release profile of an active agent from the system. The system, in one embodiment, forms a low viscosity solution that can be easily injected into the body with standard syringes and small gauge needles. In this regard, and as will be described, the selection of solvent may be used to modulate the viscosity of the composition while minimally altering the release kinetics of the active agent from the composition. In another embodiment, the selection of the solvent is used to modulate the release kinetics of the active agent from the composition without significantly altering the viscosity of the formulation.

Studies were performed that illustrate modulation of release of solvent and active agent from a polyorthoester delivery system. In one study, as detailed in Example 1, compositions comprised of a polyorthoester polymer, granisetron base, and an aprotic solvent were prepared, using as exemplary solvents dimethyl sulfoxide (DMSO) and dimethyl acetamide (DMAC). The release of solvent from the composition was measured in an in vitro dissolution release apparatus, and the results are shown in FIGS. 1A-1B.

Figure 1B:
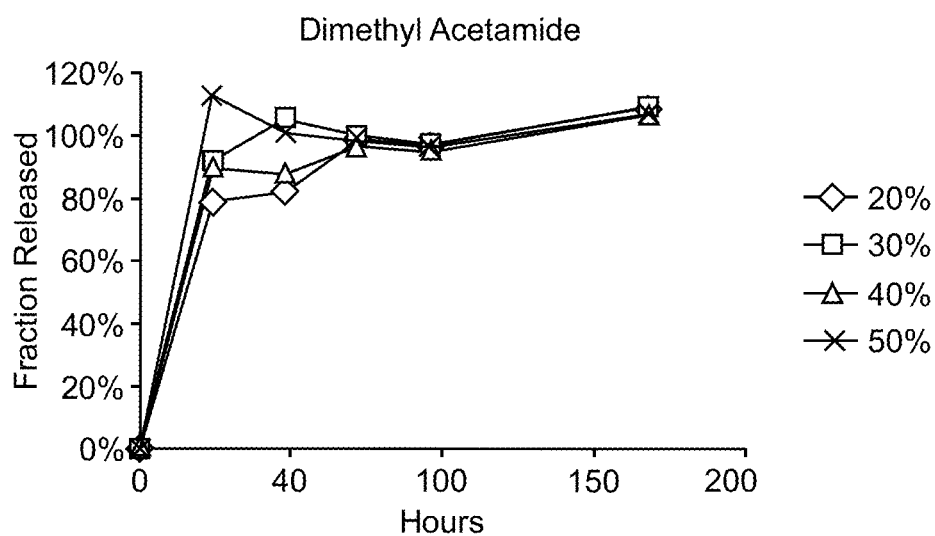

FIG. 1A shows the percent of DMSO released as a function of time, in hours, for the compositions with 30% DMSO (diamonds), 40% DMSO (squares) and 50% DMSO (triangles). FIG. 1B shows the percent DMAC released as a function of time, in hours, for the compositions with 20% DMAC (diamonds), 30% DMAC (squares), 40% DMAC (triangles), or 50% DMAC (x symbols). As can be seen, the solvent DMSO is released at a slower rate than DMAC from the compositions, indicating the solvents interact with the polyorthoester differently. For example, a composition with 30% DMSO released about 30% of the solvent at the 24 hour time point, whereas a composition comprised of DMAC released about 79% of the solvent at the 24 hour time point. This finding can be utilized to modulate release of an active agent from the compositions as provided herein in several ways. For example, an active agent that is soluble in an aprotic solvent that is released from the composition rapidly will provide for release of the active agent at a rate similar to the release of the solvent, assuming that the active agent does not alter the interaction of the solvent and the polymer. An active agent that is less soluble in an aprotic solvent that is released from the composition rapidly will release from the composition at a rate different from, and perhaps slower than, the rate of solvent release, particularly if the active agent is more soluble in the polymer than in the aprotic solvent. The data also illustrates the concept of solvent selection to tailor or modulate active agent release from a composition, in that if an active agent is equally soluble in two different solvents, the rate of release of active agent from the system can be tailored by selecting the solvent that has a faster or slower rate of release.

Figure 2A:
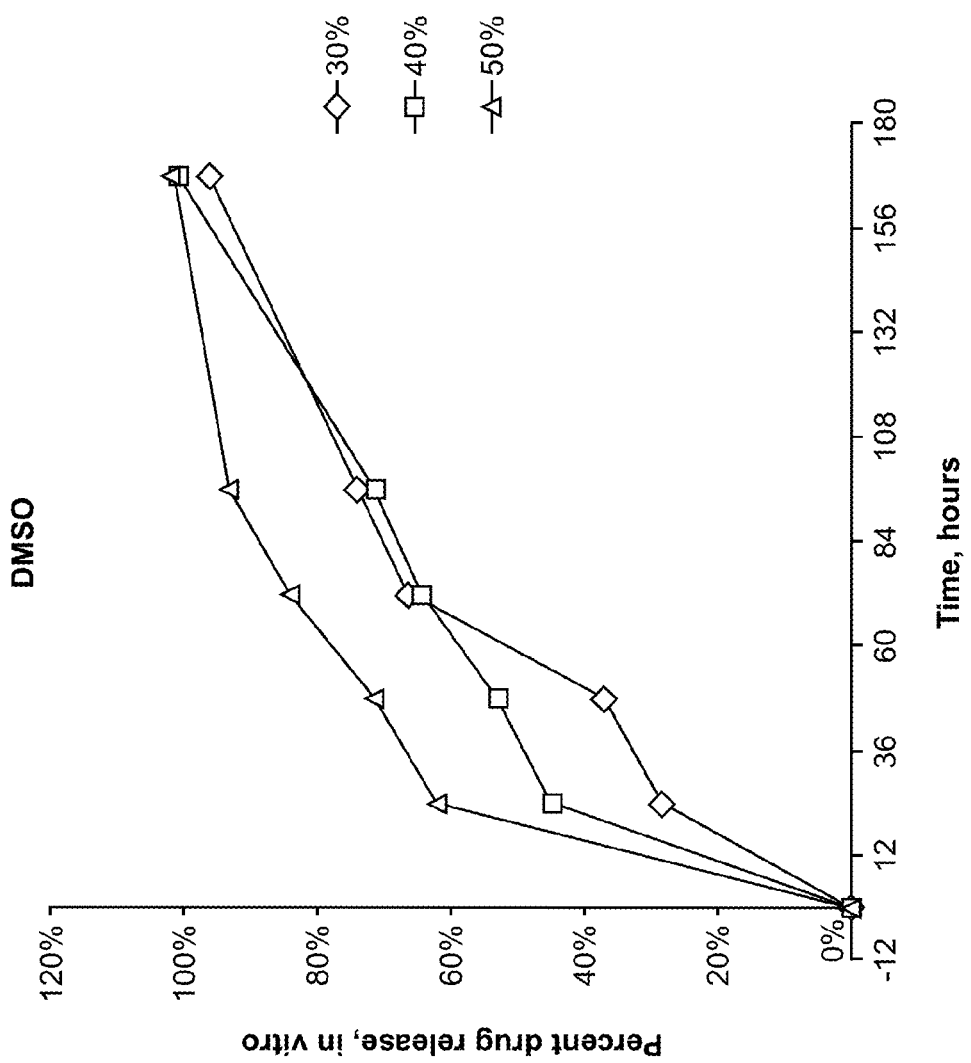
FIGS. 2A-2B are graphs of the percent of active agent, granisetron, released as a function of time, in hours, from a delivery system comprised of a polyorthoester and an aprotic solvent, dimethylsulfoxide (DMSO, FIG. 2A) or dimethyl acetamide (DMAC, FIG. 2B), in an in vitro dissolution apparatus.
Figure 2B:
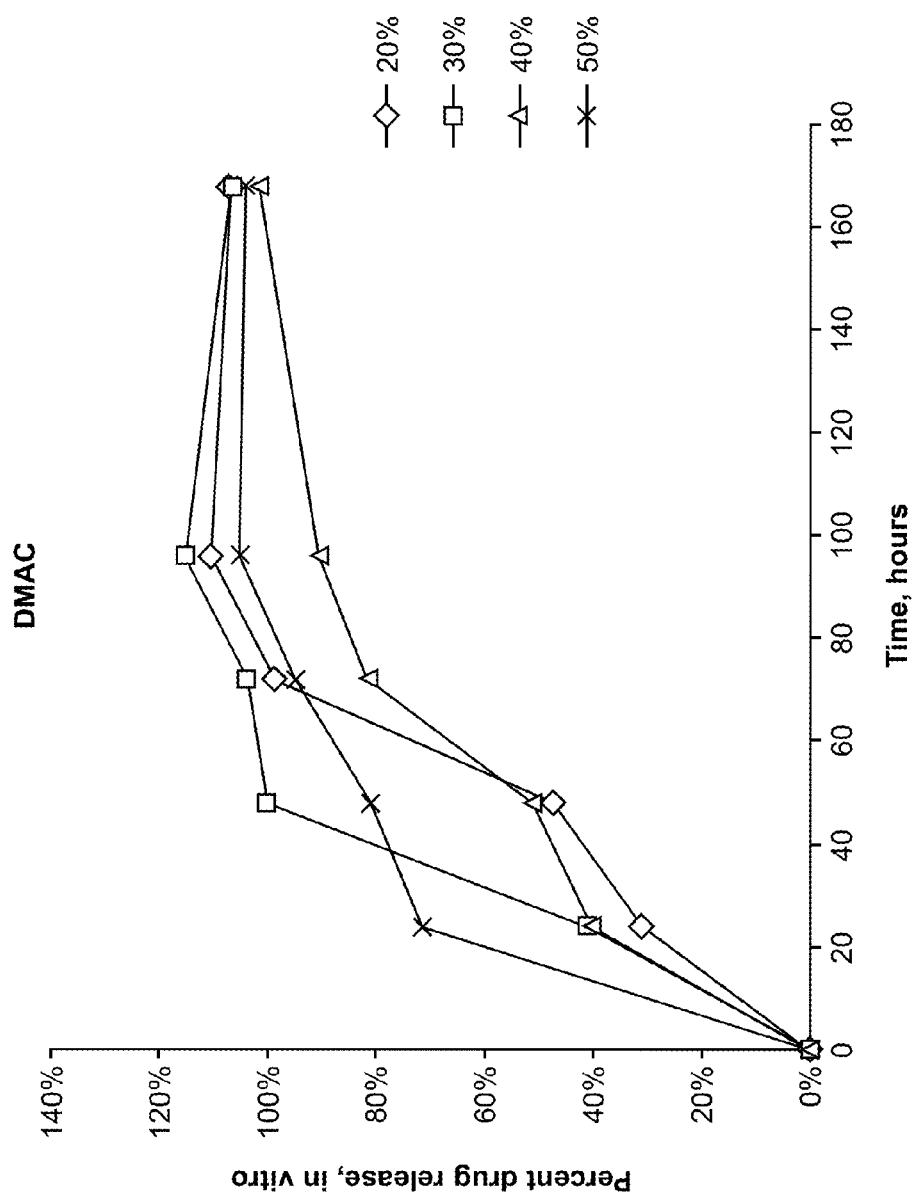

These concepts are further illustrated in the study described in Example 3. In this study a model drug, granisetron, was included in compositions comprised of a polyorthoester and an aprotic solvent, using DMSO and DMAC as exemplary solvents. The results are shown in FIGS. 2A-2B. In FIG. 2A, the in vitro release of granisetron from compositions comprising 30 wt % (triangles), 40 wt % (squares) and 50 wt % (triangles) DMSO is shown. The amount of solvent in the system influences the rate of drug release, where a higher amount of solvent in the composition achieves a higher drug release rate. This correlation is observed more strongly at release times of less than about 70 hours.

FIG. 2B shows the in vitro release of granisetron from compositions comprising 20 wt % (triangles), 30 wt % (squares), 40 wt % (triangles) and 50 wt % (x symbols) DMAC. For compositions with DMAC, the amount of solvent in the composition has less influence on the rate of granisetron release than was observed in FIG. 2A with DMSO. Compositions of a polyorthoester and 20 wt %, 30 wt % and 40 wt % DMAC released between about 30-40% of the drug at the 24 hour time point, and by 70 hours substantially all of the drug (e.g., 80-100%) from the composition was released. This system is an example of a system where rate of solvent release governs or correlates with rate of drug release. In comparing the data in FIG. 2B with that of FIG. 2A it is seen that a composition with DMSO also provides a system where drug release is correlated with rate of solvent release, however because DMSO is released from the composition more slowly than DMAC, the rate of drug release is slower, thus illustrating the versatility of the systems provided herein.

Figure 3A:
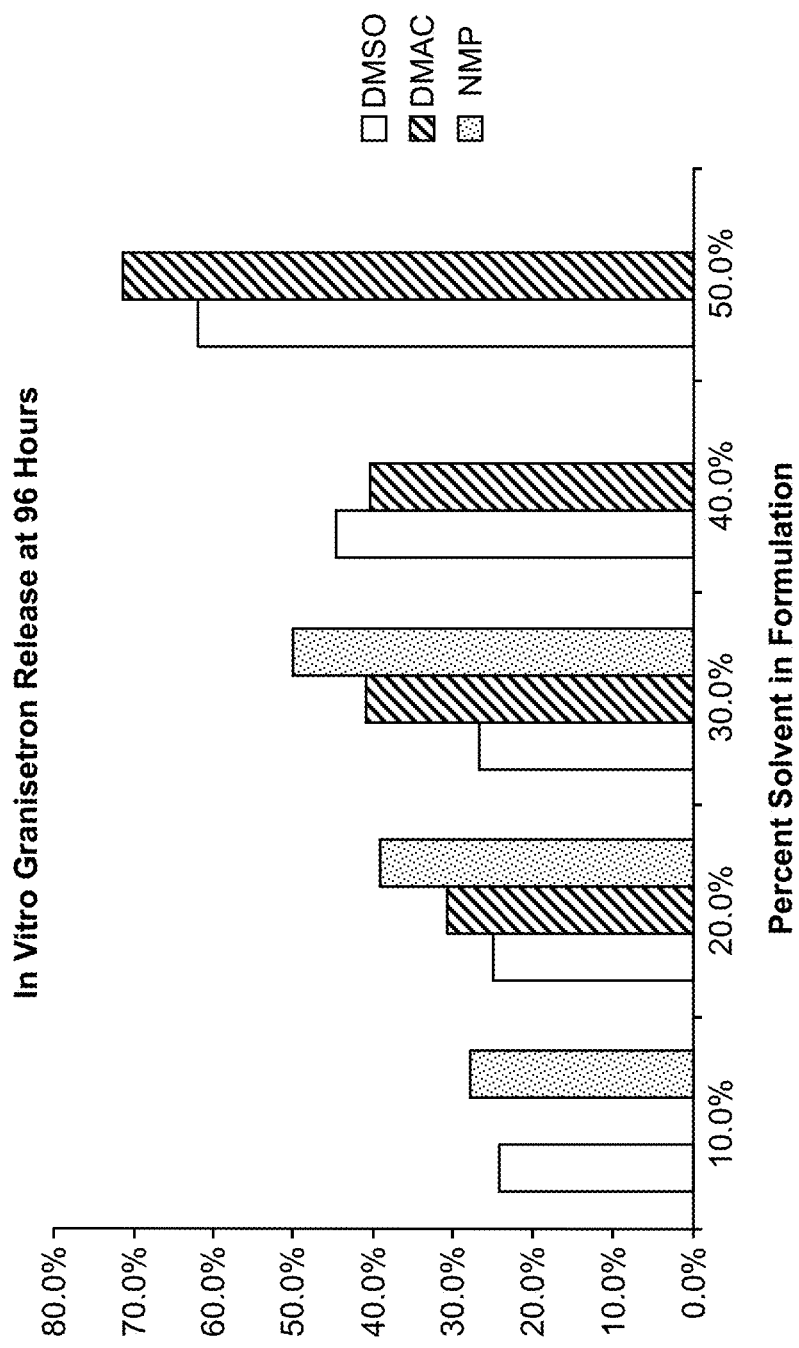
FIG. 3A is a bar graph showing the percent of active agent, granisetron, released at 24 hours in an in vitro dissolution release test, from compositions comprised of a polyorthoester and an aprotic solvent, dimethylsulfoxide (DMSO, open bars), dimethyl acetamide (DMAC, hatched bars) or N-methyl-2-pyrrolidone (NMP, dotted bars)

Another study was conducted to evaluate the release of drug from compositions comprised of a polyorthoester and the illustrative solvents DMSO, DMAC and NMP. As described in Example 4, compositions were prepared with varying amounts of solvent, and release of drug was measured in an in vitro release apparatus. FIG. 3A is a bar graph showing the percent of the drug, granisetron, released after 24 hours in an in vitro release apparatus from the compositions. The compositions with 20 wt % and 30 wt % solvent show that release of active agent from the composition depends on the solvent, where compositions with 20-30 wt % DMSO (open bars) release drug more slowly than compositions with 20-30 wt % DMAC (hatched bars), which release drug more slowly than compositions with 20-30 wt % NMP (dotted bars). Accordingly, in one embodiment, a composition comprised of a polyorthoester and greater than 10 wt % and less than 40 wt % of an aprotic solvent is contemplated, where the rate of drug release from the composition is dependent on the aprotic solvent. As seen, selection of NMP as the aprotic solvent provides a composition that releases drug more rapidly than a composition comprising either DMAC or DMSO. Selection of DMSO as the aprotic solvent for the composition provides for release of drug more slowly than a composition comprising the same polymer and drug, but comprising NMP or DMAC.

In one embodiment, the solvent in the composition remains in the composition for the period of drug delivery. Compositions where the solvent remains associated with the polymer typically provided for a rate of drug release that is within about 10%, or 20%, or 30% of the rate of solvent release over a time interval of between 2-5 hours, or 4-6 hours, 4-8 hours. In another embodiment, the solvent in the composition is released from the composition at a rate more rapidly than the drug, which remains in the polymer for a time longer than the solvent. This, second embodiment may be important where an insoluble drug is dispersed in the composition, and then the solvent rapidly leaving behind the insoluble drug actually slows the release of the drug.

Figure 3B:
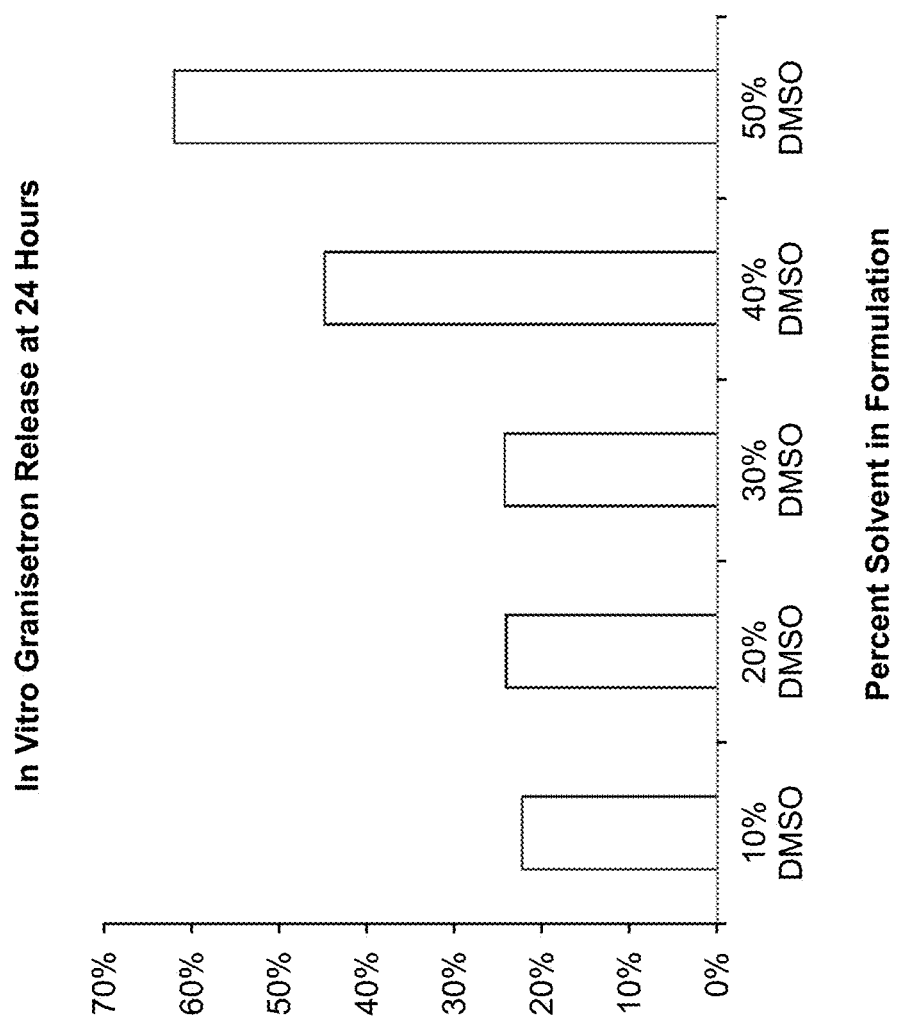

The data in FIG. 3B illustrates the effect of amount of solvent in a composition on rate of drug release. Compositions comprised of polyorthosester, the drug granisetron, and the exemplary aprotic solvent DMSO were prepared, where the percent of solvent in the formulation varied from 10 wt %-50 wt %. Release of drug was measured in an in vitro release apparatus, and the percentage of drug released in the early phase, after 24 hours, is shown in FIG. 3B. During this phase the release of granisetron from the composition is controlled by diffusion and remains relatively constant until a threshold concentration of DMSO is reached, after which, the rate of diffusion of granisetron out of the formulation increases. The percentage of drug released in a later phase, after 72 hours, is shown in FIG. 3C. During this phase the release of granisetron from the composition is controlled more by biodegradation of the composition. Drug release in this phase depends on a complex interaction of drug polymer and solvent. For the composition of 2% granisetron base, DMSO and polyorthoester, the slowest rate of release at 30% DMSO is observed.

Figure 4:
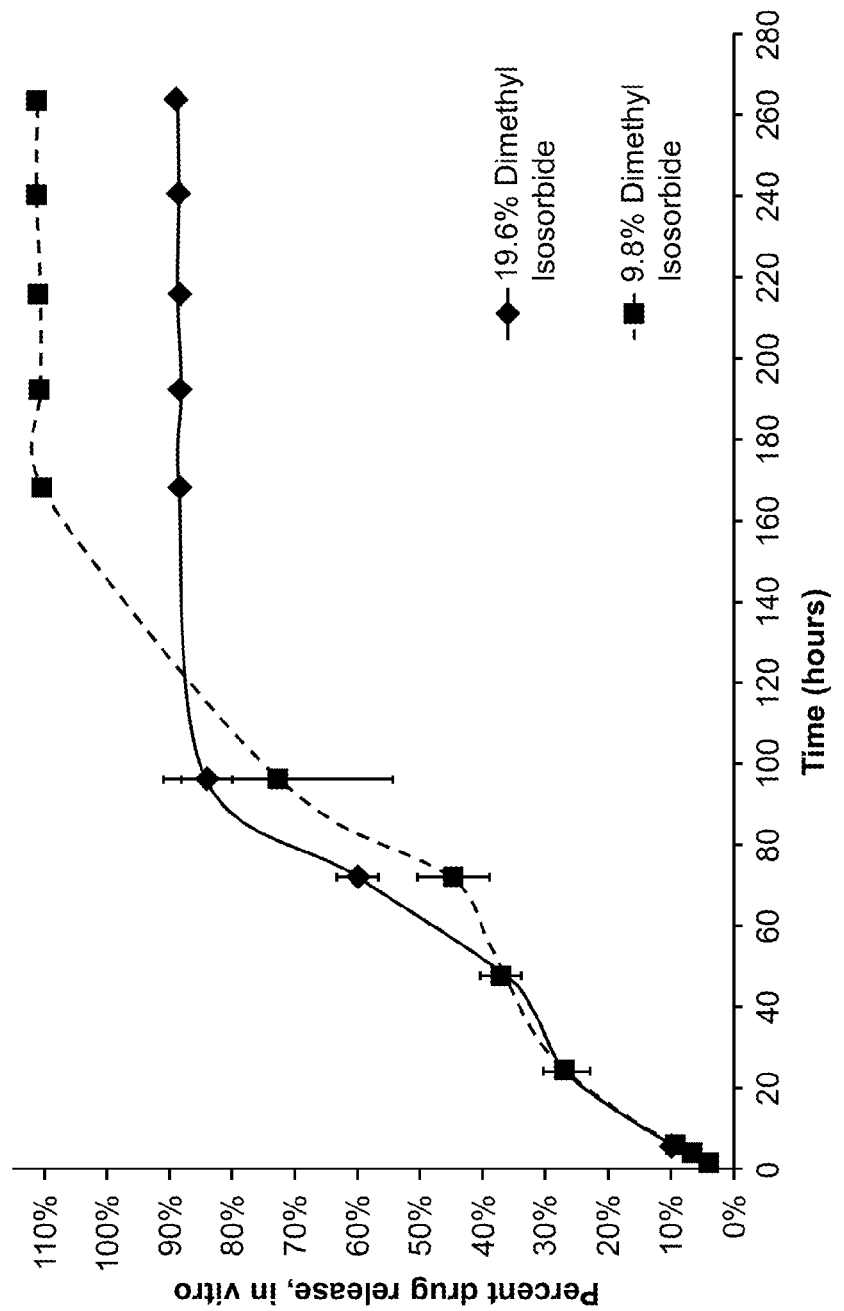
FIG. 4 is a graph of the percent of active agent, granisetron, released as a function of time, in hours, from a delivery system comprised of a polyorthoester and an aprotic solvent, dimethyl isosorbide at concentrations in the system of 19.6 wt % (diamonds) and 9.8 wt % (squares)

Another delivery system was prepared, as described in Example 4, that was comprised of a polyorthoester, the aprotic ether solvent, dimethyl isosorbide, and granisetron as the model drug. The systems were prepared with two concentrations of dimethyl isosorbide—19.6 wt % and 9.6 wt %. Release of drug from the systems was measured in vitro, and the results are shown in FIG. 4. The drug release rate observed at times less than about 30 hours was essentially the same for the two systems, with less than 30% of the drug released 24 hours after placement in the environment of use. The rate of drug release after about 40 hours increased, with the system comprising about 20 wt % solvent (diamonds) having a faster rate of release than the system with about 10 wt % solvent (squares).

Accordingly, in one embodiment, the delivery systems and compositions described herein provide a biphasic release of drug and/or solvent, where in some embodiments, release of drug and/or solvent is diffusion controlled at times less than about 48 hours, 24 hours, 6 hours, 5 hours, 4 hours, 3 hours, 2 hours and 1 hour after administration into an environment of use, and release of drug and/or solvent is controlled by or correlates with the rate of erosion of the polymer at times greater than 6 hours, 7 hours, 8 hours, 9 hours, 10 hours, 24 hours, and 48 hours after administration into an environment of use.

Further exemplary compositions and delivery systems are provided in Example 7. Illustrative compositions as provided therein comprise between 45 wt % to 80 wt % polyorthoester of formula III, between 20 wt % and 45 wt % of an aprotic solvent, and between 4 wt % to 22 wt % ropivacaine as the model therapeutic (anesthetic) agent. The aprotic solvents, dimethyl acetamide (DMAC), N-methyl-pyrrolidone (NMP), and dimethyl sulfoxide (DMSO) were included in the delivery systems investigated. One composition contained a mixture of DMSO and NMP (4.7% DMSO and 22.5% NMP). A further study, as described in Example 8, was carried out to evaluate the in-vitro release of the active agent, ropivacaine, from the compositions, when placed in phosphate buffered saline at 37° C. Release of active agent was evaluated at 24 hour intervals from 24 hours to 144 hours or more. At 24 hours, the composition with the highest percentage of ropivacaine released, 45.26%, was a formulation comprised of 24 wt % of NMP. Although this formulation released the greatest percentage of active agent within the first 24 hours, the rate of drug release slowed significantly after this point, with cumulative release of drug at only 58.65 percent at 96 hours. In contrast, a formulation similarly containing NMP as the aprotic solvent, but at 45.2 wt % (nearly twice the amount of the former formulation), released 35.78 percent active agent in the first 24 hours, and had released 86.6 wt % active agent by the 96 hour time point. A formulation comprising 28.9 wt % of NMP demonstrated a release rate of active agent similar to that observed for the 24 wt % NMP formulation. Thus, varying amounts of a given aprotic solvent impact the release profile of active agent. A formulation comprised of a mixture of DMSO and NMP as the aprotic solvent exhibited the slowest release of drug, with 8.61 wt % drug released at 24 hours, and only 34.17 wt % drug release at 96 hours. In general, DMSO-containing compositions containing similar amounts of aprotic solvent release the active agent more slowly than formulations containing similar amounts of NMP, while a DMAC-containing formulation releases active agent more slowly than a corresponding formulation comprised of similar amounts of NMP. These results are consistent with previous studies in which it was seen that selection of NMP as the aprotic solvent provides a composition that releases drug more rapidly than a composition comprising either DMAC or DMSO.

A further study was carried out, as described in Example 11, to investigate the in-vitro release of yet another amino-amide anesthetic model drug, bupivacaine, in a drug delivery system as provided herein comprising an aprotic solvent. Compositions were prepared containing between approximately 42 wt % to 60 wt % of a polyorthoester of formula III, between about 30 wt % and 42 wt % of an aprotic solvent, and between about 9 wt % and 15 wt % of the anesthetic, bupivacaine. The compositions are described generally in Example 10. In this example, NMP was used as the aprotic solvent, although any aprotic solvent as provided herein may be used. The study further demonstrates that the compositions are effective to release active agent over an extended period of time, in this case, over a period of at least 192 hours. At each time point, the amount (i.e., percentage) of active agent released from the formulation containing a smaller weight percentage of active agent was lower than that of the formulation comprised of a greater amount of active agent.

Additional studies were carried out on delivery systems comprising a polyorthoester, an aprotic solvent, and the semi-synthetic opioid, buprenorphine. In these embodiments, compositions containing between 76.2 wt % to 62.1 wt % polyorthoester of formula III, between 30.0 wt % and 42.5 wt % of an aprotic solvent, and between 4.9 and 15 wt % of s semi-synthetic opioid were prepared. See, e.g., Example 14. In this study, the model solvents DMSO and NMP were used. An in-vitro release study was carried out as described in Example 15. This study further demonstrates that the aprotic-solvent comprising formulations provided herein are effective to provide an extended release of active agent over time.

The systems and compositions provided herein include a polyorthoester polymer. A wide range of polyorthoester polymers are suitable for use in the systems and compositions provided. For instance, in one embodiment, the compositions and delivery systems described herein are comprised of a polyorthoester of formula I, formula II, formula III or formula IV:

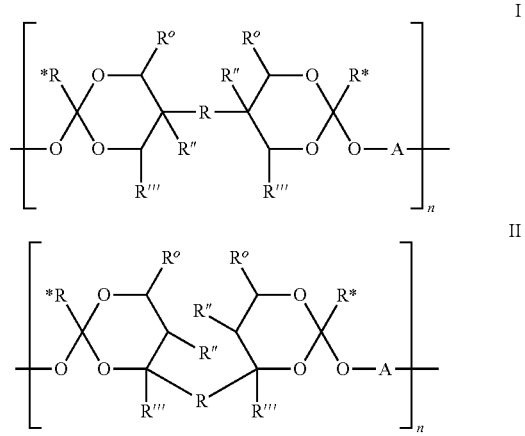

-continued

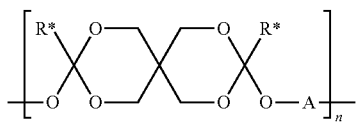
III

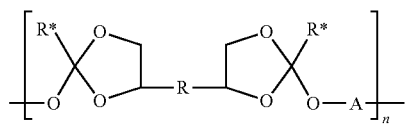
IV where:

R is a bond, —(CH$_2$)$_a$—, or —(CH$_2$)$_b$—O—(CH$_2$)$_c$—; where a is an integer of 1 to 10, and b and c are independently integers of 1 to 5;

R* is a C$_{1-4}$ alkyl;

R°, R″ and R‴ are each independently H or C$_{1-4}$ alkyl;

n is an integer of at least 5; and

A is a diol.

In another alternative embodiment, the compositions and delivery systems described herein are comprised of a polyorthoester of formula I, formula II, formula III or formula IV:

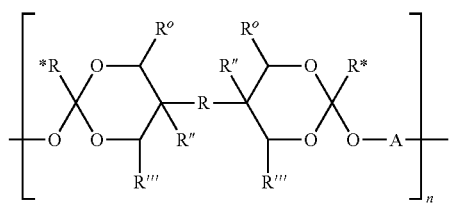
I

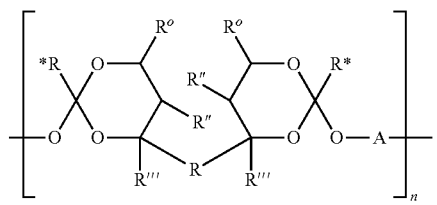
II

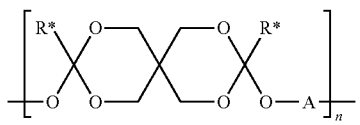
III

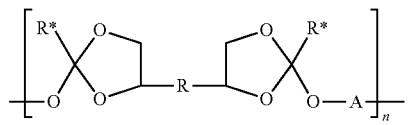
IV where:

R is a bond, —(CH$_2$)$_a$—, or —(CH$_2$)$_b$—O—(CH$_2$)$_e$—; where a is an integer of 1 to 10, and b and c are independently integers of 1 to 5;

R* is a C$_{1-4}$ alkyl;

R°, R″ and R‴ are each independently H or C$_{1-4}$ alkyl;

n is an integer of at least 5; and

A is R$^1$, R$^2$, R$^3$, or R$^4$, where

R$^1$ is:

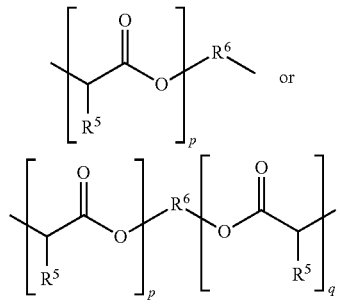

where:

p and q are integers that vary from between about 1 to 20 and the average number of p or the average of the sum of p and q is between 1 and 7 in an least a portion of the monomeric units of the polymer;

R$^5$ is hydrogen or C$_{1-4}$ alkyl; and

R$^6$ is:

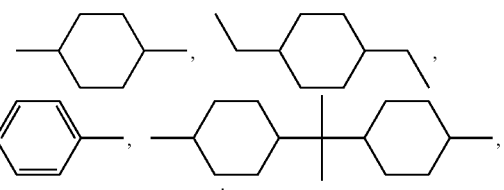

where:

s is an integer of 0 to 30;

t is an integer of 2 to 200; and

R$^7$ is hydrogen or C$_{1-4}$ alkyl;

R$^2$ is:

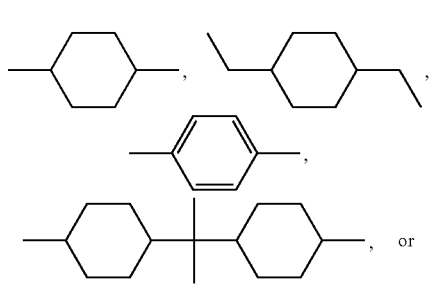

-continued

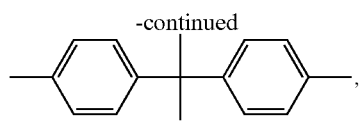

$R^3$ is:

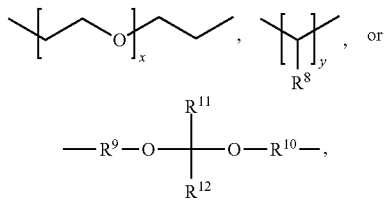

where:
x is an integer of 0 to 100;
y is an integer of 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and
$R^4$ is the residue of a diol containing at least one functional group independently selected from amide, imide, urea, and urethane groups.

Additional polyorthoesters for use herein are those in which, in certain embodiments, A is $R^1$, $R^3$, or $R^4$, where $R^1$ is:

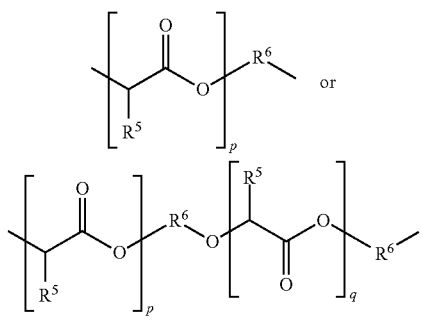

where:
p and q are integers that vary from between about 1 to 20 and the average number of p or the average of the sum of p and q is between 1 and 7 in an least a portion of the monomeric units of the polymer;
$R^3$ and $R^6$ are each independently:

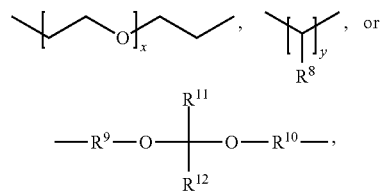

where:
x is an integer of 0 to 30;
y is an integer of 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and
$R^4$ is a residual of a diol containing at least one functional group independently selected from amide, imide, urea and urethane groups; and $R^5$ is hydrogen or $C_{1-4}$ alkyl.

In one or more preferred embodiments, the descriptions of substituents, structures, and variables as set forth in one or more of the embodiments above or below relate in particular to the polyorthoester of formula III.

In one or more embodiments, the concentration of the polyorthoester ranges from 1% to 99% by weight.

In a particular embodiments, the polyorthoester has a molecular weight between 1,000 and 10,000.

In yet another embodiment, the fraction of the A units that are of the formula $R^1$ is between about 0 and 25 mole percent.

In yet another embodiment, the fraction of the A units that are of the formula $R^1$ is between about 0 and 10 mole percent.

In yet another embodiment, the fraction of the A units that are of the formula $R^1$ is between about 0 and 5 mole percent.

In yet another embodiment, the fraction of the A units that are of the formula $R^1$ is between about 10 and 25 mole percent.

In yet another embodiment, none of the A units are of the formula $R^1$.

Additional polyorthoesters include, e.g., in another embodiment, a polyorthoester of formula III, where none of the units have A equal to $R^2$;
$R^3$ is:

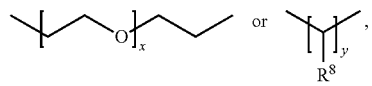

where
x is an integer of 0 to 10;
y is an integer of 2 to 30; and
$R^6$ is:

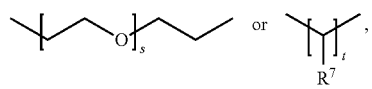

where:
s is an integer of 0 to 10;
t is an integer of 2 to 30; and
$R^5$, $R^7$, and $R^8$ are independently hydrogen or methyl.

In another embodiment, $R^3$ and $R^6$ are both —(CH$_2$CH$_2$O)$_2$(CH$_2$CH$_2$)—; $R^5$ is methyl; and p is 1 or 2.

In yet another embodiment of the polyorthoester, $R^3$ and $R^6$ are both —(CH$_2$CH$_2$O)$_9$—(CH$_2$CH$_2$)—; $R^5$ is methyl; and p or the sum of p and q is on average 2.

In another variation, the polyorthoester is of formula III, R is —(CH$_2$)$_b$O(CH$_2$)$_c$—; where b and c are both 2; $R^*$ is a C2 alkyl.

The polyorthoester, as shown in formula I, formula II, formula III and formula IV, in some embodiments, is one of alternating residues of a diketene acetal and a diol, with each adjacent pair of diketene acetal residues being separated by the residue of one polyol, such as a diol.

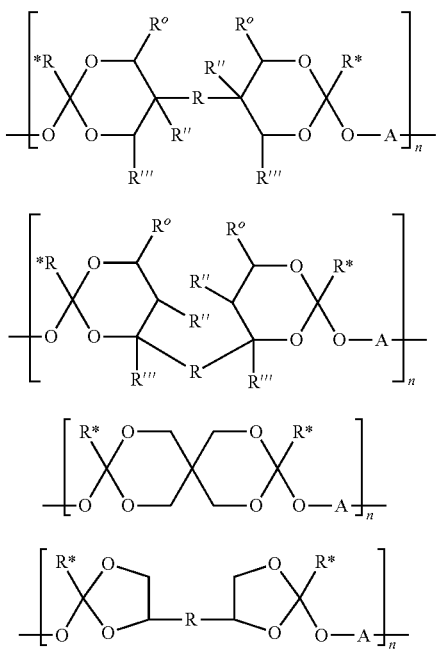

Polyorthoesters having a higher mole percentage of the "α-hydroxy acid containing" units will have a higher rate of bioerodibility. In one variation, the polyorthoesters are those in which the mole percentage of the "α-hydroxy acid containing" units is at least 0.01 mole percent, in the range of about 0.01 to about 50 mole percent, from about 0.05 to about 30 mole percent, for example from about 0.1 to about 25 mole percent, especially from about 1 to about 20 mole percent. The mole percentage of the "α-hydroxy acid containing" units appropriate to achieve the desired composition will vary from formulation to formulation.

In another embodiment, the polyorthoester is one where n is an integer of 5 to 1000; the polyorthoester has a molecular weight of 1000 to 20,000, or from 1,000 to 10,000, or from 1000 to 8000; $R^5$ is hydrogen or methyl; $R^6$ is:

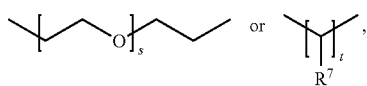

where s is an integer of 0 to 10, especially 1 to 4; t is an integer of 2 to 30, especially 2 to 10; and $R^7$ is hydrogen or methyl;
$R^3$ is:

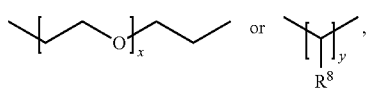

where x is an integer of 0 to 10, especially 1 to 4; y is an integer of 2 to 30, or 2 to 10; and $R^8$ is hydrogen or methyl;
$R^4$ is selected from the residue of an aliphatic diol of 2 to 20 carbon atoms, or 2 to 10 carbon atoms, interrupted by one or two amide, imide, urea or urethane groups;

the proportion of units in which A is $R^1$ is about 0-50 mol %, or 0.01-50 mol %, or 0.05-30 mol %, or 0.1-25 mol %;

the proportion of units in which A is $R^2$ is less than 20%, or less than 10%, especially less than 5%, and the proportion of units in which A is $R^4$ is less than 20%, less than 10%, or less than 5%.

In one or more additional embodiments, the polyorthoesters used in the presently disclosed delivery systems and compositions are selected from formulas III and IV below:

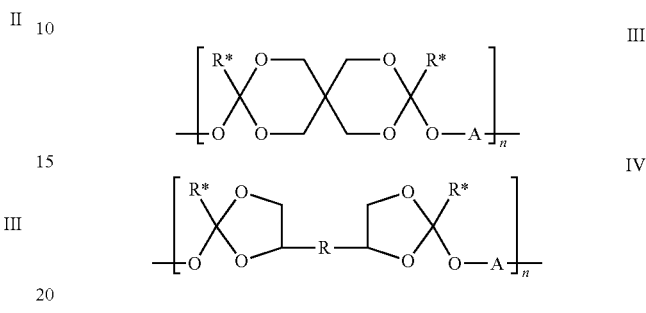

where:
R is a bond, —$(CH_2)_a$—, or —$(CH_2)_b$—O—$(CH_2)_c$—; where a is an integer from 1 to 10, and b and c are independently integers from 1-5; R* is a $C_{1-4}$ alkyl;
$R^o$, $R^{II}$ and $R^{III}$ are each independently H or $C_{1-4}$ alkyl;
n is an integer of at least 5, for example, from 5 to 1000; and
A is $R^1$, $R^2$, $R^3$, or $R^4$, where
$R^1$ is:

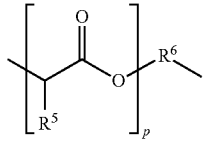

where:
p is an integer of 1 to 20;
$R^5$ is hydrogen or $C_{1-4}$ alkyl; and
$R^6$ is:

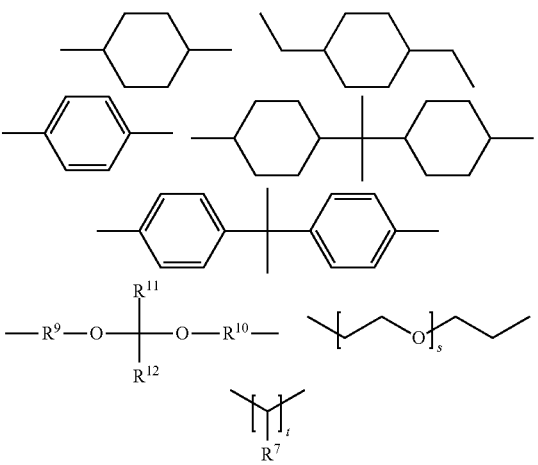

where:
s is an integer of 0 to 30;
t is an integer of 2 to 200; and
$R^7$ is hydrogen or $C_{1-4}$ alkyl;

$R^2$ is:

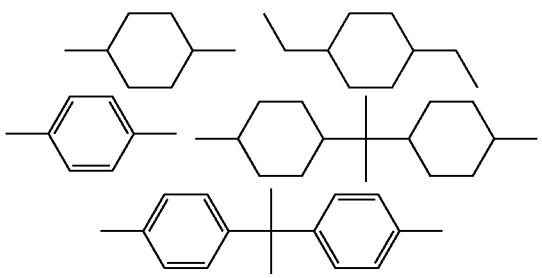

$R^3$ is:

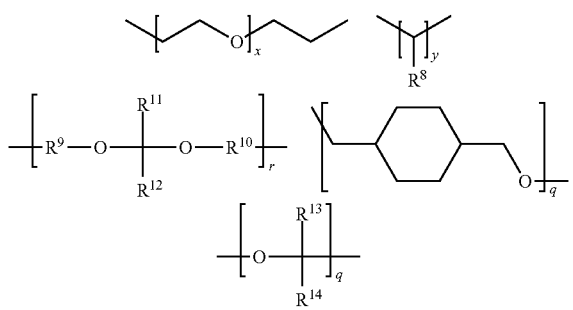

where:
x is an integer of 0 to 100;
y is an integer of 2 to 200;
q is an integer of 2 to 20;
r is an integer of 1 to 20;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R_{11}$ and $R_{12}$ together are $C_{3-10}$ alkylene; and
$R^4$ is the residue of a diol containing at least one functional group independently selected form amide, imide, urea, and urethane groups;

In one preferred embodiment related to the foregoing, the polyorthoester is described by formula III.

The polyorthoester polymers are prepared, for example, by reaction of a diketene acetal according to one of the following formulas:

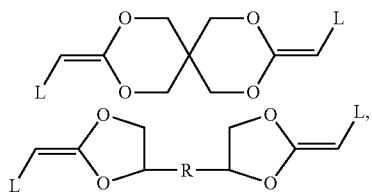

where L is hydrogen or a $C_{1-3}$ alkyl, and R is as defined above, with a at least one diol according to the formulae, HO—$R^1$—OH, HO—$R^2$—OH, HO—$R^3$—OH, or HO—$R^4$—OH (where (where $R^1$, $R^2$, $R^3$ and $R^4$ are as described above). In the presence of water, the α-hydroxy acid containing subunits are readily hydrolyzed at body temperature and at physiological pH to produce the corresponding hydroxyacids, which can then act as catalysts to control the hydrolysis rate of the polyorthoester without the addition of exogenous acid. Thus, polyorthoesters having a higher mole percentage of α-hydroxy acid containing subunits possess a higher degree of bioerodibility.

Preferred polyorthoesters are those in which the mole percentage of α-hydroxy acid containing subunits is at least about 0.01 mole percent, although in certain instances, polyorthoesters having no α-hydroxy acid-containing subunits may be employed. Exemplary percentages of α-hydroxy acid containing subunits in the polymer (e.g., glycolide-derived subunits) are from about 0 to about 50 mole percent, or from about 0.01 to about 50 mole percent, or from about 0.05 to about 30 mole percent, or from about 0.1 to about 25 mole percent. As an illustration, the percentage of α-hydroxy acid containing subunits may be 0, 1, 2, 3, 4, 5, 6, 7, 8, 9, 10, 11, 12, 13, 14, 15, 16, 17, 18, 19, 20, 21, 22, 23, 24, 24, 26, 27, 28, 29 or 30 mol percent, including any and all ranges lying therein, formed by combination of any one lower mole percentage number with any higher mole percentage number.

In one embodiment, a preferred polyorthoester is one in which $R^5$ is hydrogen or methyl; $R^6$ is

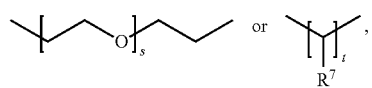

where s is an integer from 0 to 10, e.g., preferably selected from 1, 2, 3, or 4; t is an integer from 2 to 30, particularly selected from 2, 3, 4, 5, 6, 7, 8, 9 and 10; $R^7$ is hydrogen or methyl; and $R^3$ is

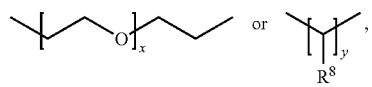

where x is an integer from 0 to 10, e.g., preferably selected from 1, 2, 3, or 4; y is an integer from 2 to 30, particularly selected from 2, 3, 4, 5, 6, 7, 8, 9 and 10; $R^8$ is hydrogen or methyl; $R^4$ is selected from a residue of an aliphatic diol having from 2-20 carbon atoms (e.g., selected from 2, 3, 4, 5, 6, 7, 8, 9, 10, 11, 12, 13, 14, 15, 16, 17, 18, 19, and 20 carbon atoms), preferably having from 2 to 10 carbon atoms, interrupted by one or two amide, imide, urea, or urethane groups. Preferably, the proportion of subunits in the polyorthoester in which A is $R^1$ is from about 0-50 mole percent, or from 0.01-50 mole percent, or from about 0.05 to about 30 mole percent, or from about 0.1 to 25 mole percent. Illustrative and preferred mole percentages include 0, 5, 10, 15, 25 and 25 mole percent of percentage of subunits in the polyorthoester in which A is $R^1$. In one preferred embodiment, the mole percent is about 20. In yet another preferred embodiment, depending on the selection of the aprotic solvent and the active agent, the proportion of subunits in which A is $R^2$ is less than 20 percent, preferably less than about 10 percent, and more preferably less than about 5 percent, and the proportion of subunits in which A is $R^4$ is less than 20 percent, preferably less than about 10 percent and more preferably less than 5 percent.

An exemplary polyorthoester comprises subunits selected from

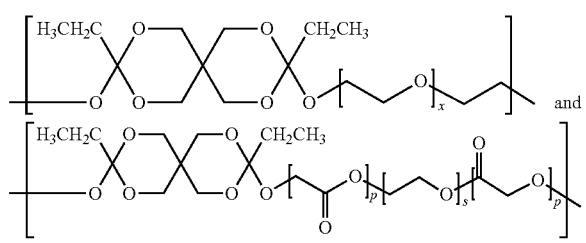

where
x is an integer from 1-4 (e.g., can be selected from 1, 2, 3, and 4)

the total amount of p is an integer from 1-20 (e.g., can be selected from 1, 2, 3, 4, 5, 6, 7, 8, 9, 10, 11, 12, 13, 14, 15, 16, 17, 18, 19, and 20), s is an integer from 1-4 (e.g., can be selected from 1, 2, 3, and 4), the mole percentage of α-hydroxyacid containing subunits in the polyorthoester is from about 0 to about 25 mole percent, or from about 0.1 to about 25 mole percent, and the polyorthoester has a molecular weight in a range of about 1,000 Da to 10,000 Da.

For example, in one embodiment, the polyorthoester comprises alternating residues of 3,9-diethyl-3,9-2,4,8,10-tetraoxaspiro[5.5]undecane-3,9-diyl:

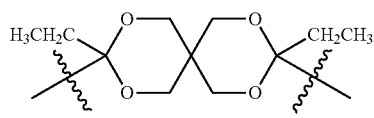

and a diol-ate residue of triethylene glycol or of triethylene glycol diglycolide prepared by reacting triethylene glycol with from 0.5 to 10 molar equivalents of glycolide at about 100-200° C. for about 12 hours to 48 hours. Typically, the mole percentage of glycolide-containing subunits in the polyorthoester is from about 0.1 to about 25 mole percent, and the polyorthoester has a molecular weight of about 1,000 Da to 10,000 Da.

Polyorthoesters such as those described above are prepared by reacting an illustrative diketene acetal, 3,9-di(ethylidene)-2,4,8,10-tetraoxaspiro[5.5]undecane (DETOSU),

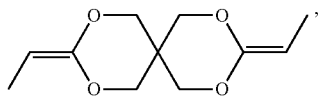

with one or more diols as described above, e.g., triethylene glycol (TEG) and triethylene glycol diglycolide (TEGdiGL). For instance, the polyorthoesters Diols such as triethylene diglycolide or triethylene monoglycolide, or the like, are prepared as described in U.S. Pat. No. 5,968,543, e.g., by reacting triethylene glcol and glycolide under anhydrous conditions to form the desired product. For example, a diol of the formula HO—$R^1$—OH comprising a polyester moiety may be prepared by reacting a diol of the formula HO—$R^6$—OH with between 0.5 and 10 molar equivalents of a cyclic diester of an α-hydroxy acid such as lactide or glycolide, and allowing the reaction to proceed at 100-200° C. for about 12 hours to about 48 hours. Suitable solvents for the reaction include organic solvents such as dimethylacetamide, dimethyl sulfoxide, dimethylformamide, acetonitrile, pyrrolidone, tetrahydrofuran, and methylbutyl ether. Although the diol product is generally referred to herein as a discrete and simplified entity, e.g., TEG diglycolide (and products such as TEG diglycolide), it will be understood by those of skill in the art that due to the reactive nature of the reactants, e.g., ring opening of the glycolide, the diol is actually a complex mixture resulting from the reaction, such that the term, TEG diglycolide, generally refers to the average or overall nature of the product. In a preferred embodiment, the polyorthoester is prepared by reacting DETOSU, triethylene glycol, and triethylene glycol diglycolide in the following molar ratios: 90:80:20. Thus, in a particular embodiment, the polyorthoester comprises about 20 mole percent $R^1$, where $R^1$ is triethylene glycol diglycolide, and 80 mole percent $R^3$, where $R^3$ is triethylene glycol.

Additional methods of manufacturing the polyorthoesters are well known in the art.

Solvents for use in the compositions and delivery systems are aprotic solvents, and can be either water miscible, partially water miscible, or poorly water miscible, depending on the desired release profile for a given active agent and the solubility of the active agent in the polyorthoester polymer and polymer/solvent combination. It is also desired that the solvent be non-toxic. In one embodiment the solvent is selected such that it will quickly leave the composition after coming into contact with an aqueous environment, e.g. body fluids. In another embodiment, the solvent is selected such that, at least, some of the solvent will remain in the composition after coming into contact with body fluids.

In some embodiments a composition is comprised of a drug dissolved in a polymer/hydrophilic (water miscible) solvent combination, and the drug may be encapsulated or entrapped in the polymer matrix as the hydrophilic solvent dissolves or dissipates from the composition and into the body fluid. In other embodiments, a composition is comprised of a lipophilic (poorly water miscible) solvent, and the dissolution or diffusion of the lipophilic solvent into surrounding aqueous tissue fluid will be relatively slow with a resultant slower increase in viscosity of the administered composition. However, a lipophilic solvent, by its own nature, may slow the release of active agent incorporated into the composition until the solvent has dissipated, leaving the polymer at the site of delivery with the entrapped active agent. By adjusting the hydrophilicity/lipophilicity character of the polymer and/or the solvent, the release of the active agent can be controlled to provide a low initial burst and sustained release of both hydrophilic and lipophilic active agents. In addition, the solubility of a hydrophilic or lipophilic active agent can be controlled to provide either solutions or dispersions of the active agent in the liquid polymer/solvent compositions.

Suitable hydrophilic (water miscible) biocompatible organic solvents that may be used have, in one embodiment, water solubility greater than 10% by weight of the solvent in water. Examples of hydrophilic biocompatible organic solvents include amides such as N-methyl-2-pyrrolidone (NMP), 2-pyrrolidone, N-ethyl-2-pyrrolidone, N-cycylohexyl-2-pyrrolidone, dimethyl acetamide, and dimethyl formamide; esters of monobasic acids such as methyl lactate, ethyl lactate, and methyl acetate; sulfoxides such as dimethyl sulfoxide and decylmethylsulfoxide; lactones such as e-caprolactone and butyrolactone; ketones such as acetone and methyl ethyl ketone; and ethers such as dimethyl isosorbide and tetrahydrofuran.

Suitable lipophilic biocompatible organic solvents that may be used in the compositions and delivery systems described herein have, in one embodiment, a water solubility less than 10% by weight of the solvent in water. Examples of lipophilic biocompatible organic solvents include esters of mono-, di-, and tricarboxylic acids such as ethyl acetate, ethyl oleate and isopropyl myristate; and esters of aromatic acids such as benzyl benzoate.

Combinations of different hydrophilic solvents can be used to obtain higher or lower levels of solubility of the liquid polymer and bioactive agent in the resultant solution. A combination of organic solvents can also be used to control the rate of release of an active agent by controlling the rate at which the solvent dissolves or dissipates when the liquid polymer/solvent/active agent composition is placed in the body. Similarly, combinations of different lipophilic solvents can also be used to control the solubility of the liquid polymer and active agent in the solvent and the release of the active agent in the body. In other embodiments, combinations of hydrophilic and lipophilic solvents can be used to obtain the optimum solvent characteristics for a delivery system. Examples include a combination of N-methylpyrrolidone and isopropyl myristate which provides a more hydrophobic solvent than N-methylpyrrolidone alone, and a combination of N-methylpyrrolidone and another more soluble organic solvent, to provide a more hydrophilic solvent combination than N-methylpyrrolidone alone.

In one embodiment, the solvent is not one or more of the following solvents: propylene glycol dicaprate, propylene glycol dicaprylate, glycofurol, a non- or partially-hydrogenated vegetable oil, glyceryl caprylate, glyceryl captate, glyceryl caprylate/caprate, glyceryl 10 caprylate/caprate/laurate, poly(ethylene glycol-copolypropylene glycol, poly(ethylene glycol)monomethyl ether 550, poly(ethylene glycol)dimethyl ether 250, glycerine triacetate, or a triglyceride.

The organic solvent is typically added to the compositions in an amount ranging from about 10 percent to about 70 percent by weight, relative to the total weight of the composition. The solvent may be present in the composition in an amount ranging from about 20 percent to about 50 percent or from about 15 percent to about 40 percent by weight, depending upon the particular solvent, the polyorthoester, active agent and desired release profile of the therapeutic agent. In other embodiments, the solvent may be present in the composition in an amount ranging from about 10-60 wt %, 15-60 wt %, 15-50 wt %, 20-60 wt %, 25-50 wt %, 30-70 wt %, 30-60 wt %, 30-50 wt %, 35-70 wt %, 35-60 wt %, 35-50 wt %, 10-20 wt %, 15-25 wt %, 20-30 wt %, 15-35 wt %, 20-35 wt % or 20-40 wt %. The concentration of solvent allows for the level of polymer in the composition to range from about 30 percent to about 90 percent by weight, or from about 50 percent to about 80 percent by weight relative to the overall composition.

In other embodiments, the compositions comprise between about 10 percent by weight to about 70 percent by weight solvent, relative to the combined weight of the polymer and solvent in the composition, or the compositions may comprise between about 20-50 or 15-40 percent by weight solvent, relative to the combined weight of the polymer and solvent in the composition. In other embodiments, the solvent may be present in the composition in an amount, relative to the combined amount of polymer and solvent in the composition, ranging from about 10-60 wt %, 15-60 wt %, 15-50 wt %, 20-60 wt %, 25-50 wt %, 30-70 wt %, 30-60 wt %, 30-50 wt %, 35-70 wt %, 35-60 wt %, 10-20 wt %, 15-25 wt %, 20-30 wt %, 15-35 wt %, 20-35 wt % or 20-40 wt %. The concentration of solvent may allow for the level of polymer in the composition to range from about 30 percent to about 90 percent by weight, or from about 50 percent to about 80 percent by weight relative to weight of the polymer and solvent in the composition.

The polymer/solvent concentrations permit the liquid polymer/solvent compositions to be easily injected with standard syringes and small gauge needles (e.g., about 18-26 gauge) unlike liquid polymer formulations previously described, for example, which in some embodiments, unlike the present compositions, require the addition of a particulate material to achieve an acceptable viscosity for injection with a syringe and needle. The compositions of the invention can be administered into the body of a human subject or animal such as a dog, cat, horse, etc.

The rate of release of the active agent (e.g., drug) can be controlled by the composition of the biodegradable polymer and/or by the hydrophilicity or lipophilicity of the organic solvent that is used. The composition of the liquid polymer (i.e., the type of monomer used or the ratio of monomers for copolymers or terpolymers, the end groups on the polymer chains, and the molecular weight of the polymer) will determine the hydrophilicity or lipophilicity of the liquid polymer material as well as the degradation time of the liquid polymer depot. More hydrophilic liquid polymers (e.g., polyorthoesters wherein the diol monomer is hydrophilic, e.g., triethylene glycol, tetraethylene glycol, or polyethylene glycol and the like) and/or more hydrophilic solvents (e.g., N-methyl-2-pyrrolidone) can be used for active agents in applications where faster release rates and shorter durations of release (e.g., about 1-3 days) are needed. For slower releasing active agents and where longer durations of release for prolonged delivery (e.g., about 7-90 days) are desired, more hydrophobic and slower degrading liquid polymers (polyorthoesters wherein the diol monomer is hydrophobic, e.g., 1-6 hexanediol, 1-10 decanediol, or 1-12 dodecandiol and the like) and/or more lipophilic solvents (e.g., isopropyl myristate) can be used to that advantage. For even slower rates and longer durations of release of an active agent, the active agent itself can be made more water-insoluble by utilizing active agents, for example, in the form of lipophilic salts, drug complexes, and/or prodrug esters, amides or ethers. Thus, various forms of the drug can be used as needed. The composition includes the active agent in an amount effective to provide the desired therapeutic effect over the release period. The concentration range of the active agent in the composition will vary, for example, according to the active agent, the fat ululation and the rate of release from the depot, and can range, for example, from about 0.1% to about 30% by weight. The liquid composition releases an effective amount of the bioactive agent by diffusion or dissolution from the composition as it biodegrades in the body.

While the singular form is used to describe the polyorthoester and solvent in this application, it is understood that more than one polyorthoester and/or more than one solvent selected from the groups described above may be used in the delivery system. In some embodiments of the above methods, the compositions further comprise an excipient, and in a preferred embodiment the excipient is one that does not influence the release of solvent and/or active agent from the composition. The concentrations of the polyorthoester and an excipient in the delivery vehicle may vary. For example, the concentration of an excipient in the vehicle may be in the range of 1-99% by weight, or 5-80% weight, or 20-60% by weight of the vehicle. While the singular form is used to describe the polyorthoester and excipient herein, it is understood that more than one polyorthoester and excipient may be used in the delivery system or composition. It is also understood that while not required, other pharmaceutically acceptable inert agents such as coloring agents and preservatives may also be incorporated into the composition.

Generally, the excipients are pharmaceutically acceptable and polyorthoester-compatible materials. In one embodiment, the excipient is a liquid at room temperature, and is readily miscible with the polyorthoester.

The compositions described herein are easily syringable or injectable, meaning that they can readily be dispensed from a conventional tube of the kind well known for topical or ophthalmic formulations, from a needleless syringe, or from a syringe with a 16 gauge or smaller needle (such as 16-25 gauge), and injected subcutaneously, intradermally or intramuscularly. The formulations may be applied using various methods known in the art, including by syringe, injectable or tube dispenser.

Non-limiting examples of preferred aprotic solvents are set forth in Table 1.

TABLE 1

Exemplary Aprotic Solvents

| Solvent | Class | Water Miscibility | Dipole Moment (D) |
|---|---|---|---|
| 2-pyrrolidone | amides | | 3.5 |
| dimethyl formamide | | water miscible | 3.86 |
| N-methyl-2-pyrrolidone (NMP) | | water miscible | 4.09 |
| n-ethyl-2-pyrrolidone | | water miscible | 4.1 |
| dimethyl acetamide | | water miscible | 4.60 |
| N-cyclohexyl-2-pyrrolidone | | poorly miscible | |
| caprolactam (cyclic amide) | | | |
| ethyl acetate | esters of a carboxylic acid | partially miscible (8.3 g/100 ml) | 1.84 |
| benzyl benzoate | | poorly miscible | 2.06 |
| methyl acetate | | water miscible | 1.75 |
| isopropyl myristate | Esters of a fatty acid | poorly miscible | |
| ethyl oleate | | poorly miscible | |
| methyl lactate | Esters of an acid (monobasic acid) | water miscible | |
| ethyl lactate | | water miscible | |
| propylene carbonate (4-methyl-1,3-diololan-2-one) | Esters of an alcohol (polyhydroxy alcohol) | water miscible | 4.9 |
| dimethyl ether | ethers | | 1.25 |
| tetrahydrofuran | | water miscible | 1.75 |
| methyl ethyl ketone | ketones | water miscible (27.5 g/100 mL) | 2.76 |
| acetone | | water miscible | 2.77 |
| butyrolactone | lactones | water miscible | 4.12 |
| ester-caprolactone | | water miscible | 3-4 |
| dimethyl sulfoxide | sulfoxides | water miscible | 3.9 |
| decylmethylsulfoxide | | | 3.96 |

In one embodiment, the aprotic solvent is a solvent with a dipole moment of greater than about 2 D, or greater than about 2.2 D, or greater than about 2.4 D. In one embodiment, the aprotic solvent is a solvent with a dipole moment of greater than about 2 D, or greater than about 2.2 D, or greater than about 2.4 D and is water miscible. In another embodiment, the aprotic solvent is a solvent with a dipole moment of greater than about 2 D, or greater than about 2.2 D, or greater than about 2.4 D and is poorly miscible in water. In one embodiment, a solvent is miscible with water if it forms a homogeneous solution with water in all proportions at room temperature (20-25° C.). A solvent is partially miscible if it forms a homogeneous solution with water in some proportions at room temperature (20-25° C.). A solvent is poorly miscible if it does not form a homogeneous solution with water (20-25° C.).

The release of active agents from these polyorthoester and solvent compositions often demonstrates a biphasic behavior. There can be an early phase release of active agent followed by a later phase release of active agent. In one embodiment, the release of the active agent in the early phase can be controlled by the diffusion of the drug out of the composition while drug release in the later phase can be controlled by the biodegradation of the polymer. The diffusional phase and the erosional phase of release of the active agent can be separated in time or partially overlap or completely overlap.

In one embodiment, the solvent is selected to rapidly leave the composition. In this case, release of active agent at early time points is moderated by the presence and nature of the solvent in the composition and release of the active agent at later time points is moderated by the nature of the polymer. In another embodiment, the solvent is selected to slowly leave the composition. In this case, release of the active agent from the composition is moderated by both the presence and nature of the solvent and the presence and nature of the polymer.

In another embodiment, the solvent may be selected in order to provide desired release kinetics of an active agent from the composition. The solvent may be selected to provide for a larger initial release of drug; for example, an initial drug release of about 25-40% in the first 2-5 hours, and a slower release thereafter. Alternately, the solvent may be selected to provide a more zero order (linear) kinetic release profile; for example, a release of 10% of drug within 1-3 hours, and a slow continuous zero order release thereafter until the system is depleted of drug.

It has been found that the effect of the solvent on the release rate of an active agent from the composition and the viscosity of the composition are generally independent. The viscosity of the composition can be adjusted by the addition of more solvent to reduce the viscosity and less solvent to increase the viscosity. The viscosity of the composition can also be modified by the selection of solvent. However, depending upon the nature of the solvent, these changes often have a minimal impact on the rate of release of an active agent. It has also been recognized that the compositions and delivery systems provided herein surprisingly possess a greater stability over time with respect to the polyorthoester component, i.e., the degradability thereof, when compared to compositions and delivery systems comprising a protic solvent such as polyethylene glycol, such that the release profiles of the active agent are well maintained over time.

An "active agent" or "active ingredient" refers to any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents. Suitable pharmaceutical agents include locally or systemically acting pharmaceutically active agents which may be administered to a subject by topical or intralesional application (including, for example, applying to abraded skin, lacerations, puncture wounds, etc., as well as into surgical incisions) or by injection, such as subcutaneous, intradermal, intramuscular, intraocular or intra-articular injection. Suitable pharmaceutical agents include polysaccharides, DNA and other polynucleotides, antisense oligonucleotides, antigens, antibodies, vaccines, vitamins, enzymes, proteins, naturally occurring or bioengineered substances, and the like, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids and the like), opioids (e.g. buprenorphine, butorphanol, dezocine, meptazinol, nalbuphine, oxymorphone and pentazocine), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors and the like), antipsychotic agents (for example, phenothiazines including chlorpromazine, triflupromazine, mesoridazine, piperacetazine and thioridazine; thioxanthenes including chlorprothixene and the like), anti-angiogenic agents (e.g., combresiatin, contortrostatin, anti-VEGF and the like), anti-anxiety agents (for example, benzodiazepines including diazepam, alprazolam, clonazepam, oxazepam; and barbiturates), antidepressants (including tricyclic antidepressants and monoamine oxidase inhibitors including imipramine, amitriptyline, doxepin, nortriptyline, amoxapine, tranylcypromine, phenelzine and the like), stimulants (for example, methylphenidate, doxapram, nikethamide and the like), narcotics (for example, buprenorphine, morphine, meperidine, codeine and the like), analgesic-antipyretics and anti-inflammatory agents (for example, aspirin, ibuprofen, naproxen and the like), local anesthetics (e.g., the amide- or anilide-type local anesthetics such as bupivacaine, levobupivacaine, dibucaine, mepivacaine, procaine, lidocaine, tetracaine, ropivacaine, and the like), fertility control agents, chemotherapeutic and anti-neoplastic agents (for example, mechlorethamine, cyclophosphamide, 5-fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen and the like), cardiovascular and anti-hypertensive agents (for example, procainamide, amyl nitrite, nitroglycerin, propranolol, metoprolol, prazosin, phentolamine, trimethaphan, captopril, enalapril and the like), drugs for the therapy of pulmonary disorders, anti-epilepsy agents (for example, phenyloin, ethotoin and the like), anti-hidrotics, keratoplastic agents, pigmentation agents or emollients, antiemetic agents (such as ondansetron, granisetron, tropisetron, metoclopramide, domperidone, scopolamine and the like). The composition of the present application may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agents" further includes biocides such as fungicides, pesticides and herbicides, plant growth promoters or inhibitors, preservatives, disinfectants, air purifiers and nutrients. Pro-drugs and pharmaceutically acceptable salts of the active agents are included within the scope of the present application.

In one embodiment, the active agent is an antiemetic agent. Exemplary amtiemetic agents include 5-HT$_3$ antagonists, dopamine antagonists, anticholinergic agents, GABA$_B$ receptor agonists, NK$_1$ receptor antagonists, and GABA$_A$alpha$_2$ and/or alpha$_3$ receptor agonists. In one embodiment the active agent is a 5-HT$_3$ antagonist selected from the group consisting of ondansetron, granisetron and tropisetron.

In another embodiment, the active agent is an anesthetic, e.g., an amino amide anesthetic, where the composition is designed to comprise an aprotic solvent in an amount effective to provide a rate of release of anesthetic effective for reducing or preventing pain. Representative anesthetics include bupivacaine, levobupivacaine, dibucaine, mepivacaine, procaine, lidocaine, tetracaine, and ropivacaine. In one particular embodiment, the anesthetic is ropivacaine or bupivacaine.

In yet a further embodiment, the active agent is an opioid such as buprenorphine.

The active agent or agents can be dissolved or dispersed into the composition comprising a polyorthoester and a biocompatible solvent. The concentration of the active agent in the composition may vary from about 1 wt % to 20 wt %, 1 wt % to 10 wt %, 10 wt % to 20 wt %, 2 wt % to 5 wt %, 10 wt % to 15%, or 15 wt % to 20 wt % and may be 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, 5 wt %, 5 wt %, 5.1 wt %, 5.2 wt %, 5.3 wt %, 5.4 wt %, 5.5 wt %, 5.6 wt %, 5.7 wt %, 5.8 wt %, 5.9 wt %, 6 wt %, 6.1 wt %, 6.2 wt %, 6.3 wt %, 6.4 wt %, 6.5 wt %, 6.6 wt %, 6.7 wt %, 6.8 wt %, 6.9 wt %, 7 wt %, 7.1 wt %, 7.2 wt %, 7.3 wt %, 7.4 wt %, 7.5 wt %, 7.6 wt %, 7.7 wt %, 7.8 wt %, 7.9 wt %, 8 wt %, 8.1 wt %, 8.2 wt %, 8.3 wt %, 8.4 wt %, 8.5 wt %, 8.6 wt %, 8.7 wt %, 8.8 wt %, 8.9 wt %, 9 wt %, 9.1 wt %, 9.2 wt %, 9.3 wt %, 9.4 wt %, 9.5 wt %, 9.6 wt %, 9.7 wt %, 9.8 wt %, 9.9 wt %, 10 wt %, 11 wt %, 11.1 wt %, 11.2 wt %, 11.3 wt %, 11.4 wt %, 11.5 wt %, 11.6 wt %, 11.7 wt %, 11.8 wt %, 11.9 wt %, 12 wt %, 12.1 wt %, 12.2 wt %, 12.3 wt %, 12.4 wt %, 12.5 wt %, 12.6 wt %, 12.7 wt %, 12.8 wt %, 12.9 wt %, 13 wt %, 13.1 wt %, 13.2 wt %, 13.3 wt %, 13.4 wt %, 13.5 wt %, 13.6 wt %, 13.7 wt %, 13.8 wt %, 13.9 wt %, 14 wt %, 14.1 wt %, 14.2 wt %, 14.3 wt %, 14.4 wt %, 14.5 wt %, 14.6 wt %, 14.7 wt %, 14.8 wt %, 14.9 wt %, 15 wt %, 15 wt %, 15.1 wt %, 15.2 wt %, 15.3 wt %, 15.4 wt %, 5.5 wt %, 15.6 wt %, 15.7 wt %, 15.8 wt %, 15.9 wt %, 16 wt %, 16.1 wt %, 16.2 wt %, 16.3 wt %, 16.4 wt %, 16.5 wt %, 16.6 wt %, 16.7 wt %, 16.8 wt %, 16.9 wt %, 17 wt %, 17.1 wt %, 17.2 wt %, 17.3 wt %, 17.4 wt %, 17.5 wt %, 17.6 wt %, 17.7 wt %, 17.8 wt %, 17.9 wt %, 18 wt %, 18.1 wt %, 18.2 wt %, 18.3 wt %, 18.4 wt %, 18.5 wt %, 18.6 wt %, 18.7 wt %, 18.8 wt %, 18.9 wt %, 19 wt %, 19.1 wt %, 19.2 wt %, 19.3 wt %, 19.4 wt %, 19.5 wt %, 19.6 wt %, 19.7 wt %, 19.8 wt %, 19.9 wt %, 20 wt %.

The compositions may comprise a second active agent. In one embodiment, a first and second antiemetic agent is included in the composition. In one variation, the second antiemetic agent is selected from the group consisting of alpha-2 adrenoreceptor agonists, a dopamine antagonist, an anticholinergic agent, a GABA$_B$ receptor agonist, an NK$_1$ receptor antagonist, and a GABA$_A$alpha$_2$ and/or alpha$_3$ receptor agonist. In another variation, the alpha-2 adreno-receptor agonists is selected from the group consisting of clonidine, apraclonidine, para-aminoclonidine, brimonidine, naphazoline, oxymetazoline, tetrahydrozoline, tramazoline, detomidine, medetomidine, dexmedetomidine, B-HT 920, B-HIT 933, xylazine, rilmenidine, guanabenz, guanfacine, labetalol, phenylephrine, mephentermine, metaraminol, methoxamine and xylazine.

In another aspect, the compositions and systems described herein are for treatment of a subject, and the composition or system is administered via injection to a subject in need.

In one embodiment, the compositions are for use in a method for the treatment of emesis induced by a chemotherapeutic agent, by radiation-induced nausea and vomiting, and/or by post-operative induced nausea and vomiting in a patient. The treatment includes administering to the patient a composition comprising an anti-emetic, such as a 5-HT$_3$ antagonist, where the composition is designed to include an aprotic solvent that yields a rate of release for effective anti-emetic therapy.

In another embodiment, the compositions are for use in a method of providing local anesthesia to a patient in need. The treatment includes administering to a patient a composition comprising an anesthetic, e.g., an amino amide anesthetic such as ropivacaine or bupivacaine, where the composition is designed to comprise an aprotic solvent in an amount effective to provide a rate of release of anesthetic effective for reducing or preventing pain. Local administration can be, e.g., at a nerve, into the epidural space, intrathecal, or directly to a surgical site or wound.

One further embodiment also provides a method of providing regional aesthesia to a subject by administering a composition comprising an anesthetic, e.g., an amino amide anesthetic such as ropivacaine or bupivacaine, in a region of tissue near a nerve to provide a local or regional nerve block. The dosages can be administered either as a nerve block (including acting as a motor block), or as a sensory block.

In yet another embodiment, the compositions and delivery systems provided herein are for reducing or treating acute or chronic pain. The treatment includes administering to a patient a composition comprising an opioid, such as buprenorphine or another opioid, where the composition is designed to comprise an aprotic solvent in an amount effective to provide a rate of release of the opioid effective for reducing or preventing pain.

More generally, the compositions and systems are administered to a subject (e.g., patient) in need of a treatment or prevention of a condition, in an effective amount of the flowable composition described herein. The compositions provide the advantages of liquid application to form medical or surgical devices and/or delivery systems for active agents (e.g., drugs). The present liquid polymer/solvent compositions also allow the use of smaller gauge needles compared to other liquid polymer systems made without a solvent. The solvents used in the present compositions allow an active agent to also be administered as a solution in contrast to liquid polymer systems made without solvents. The use of liquid biodegradable polymers in the present system also allows the rate of release of an active agent and degradation of the flowable composition to be varied over a wide range in contrast to the non-polymeric flowable compositions.

Figure 5:
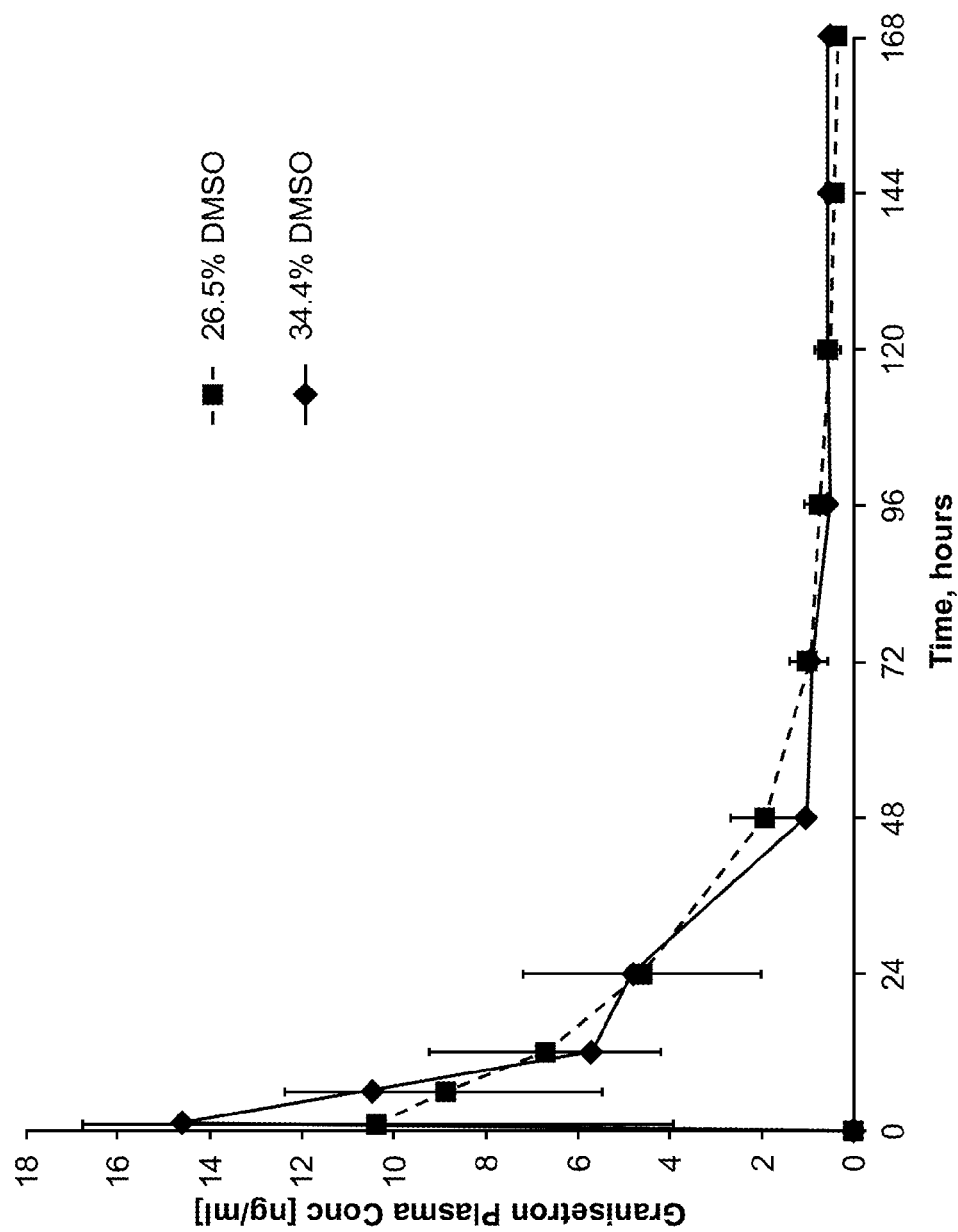
FIG. 5 is a graph of plasma concentration of granisetron, in ng/mL, as a function of time, in hours, for a delivery system comprised of a polyorthoester, granisetron, and 26.5 wt % of DMSO (squares) or 34.3 wt % DMSO.

An in vivo study was conducted to evaluate release of an active agent from a delivery system comprised of a polyorthoester and an aprotic solvent, using DMSO as the exemplary solvent. Example 6 describes the delivery system and the protocol. Plasma samples were taken from each dog in the study 24 hours before administration of a delivery system, and after administration at the following time points: 1, 6, 12, 24, 48, 72, 96, 120, 144, and 168 hours. The treatment was repeated 2 weeks later with a slightly different delivery system, and plasma samples were again taken. The plasma concentration of the active agent in the delivery systems, granisetron, as a function of time, in hours, is shown in FIG. 5. Both formulations provided measurable plasma concentrations of granisetron for at least 5 days. The formulation with the higher amount (34.3%) of DMSO gave a higher Cmaxthan did the formulation with the lower amount (26.5 wt %) DMSO.

Figure 6:
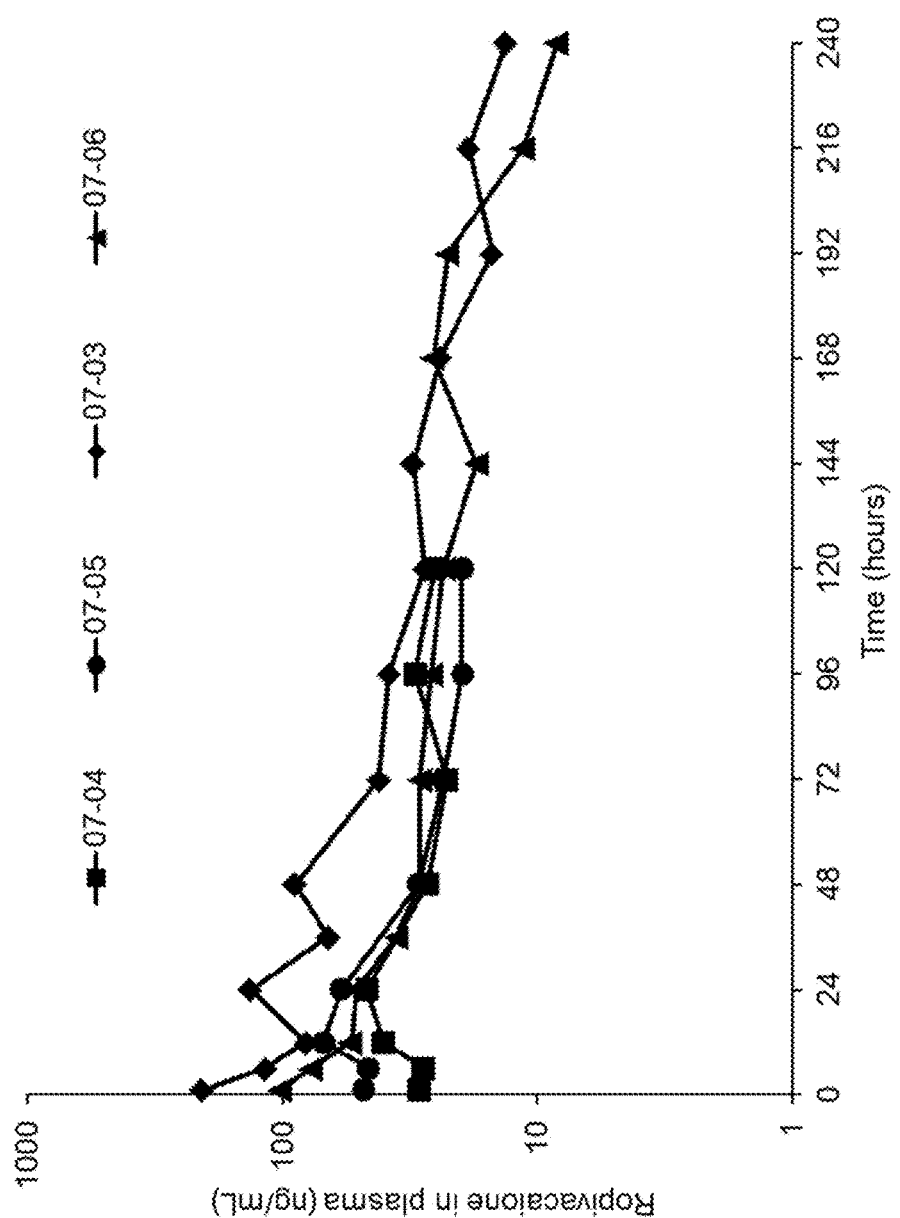
FIG. 6 is a graph of plasma concentration of ropivacaine, in ng/mL, in dogs, as a function of time, in hours, for various exemplary delivery systems comprising a polyorthoester, ropivacaine, and an aprotic solvent as described in Example 9. Data is provided for Formulation No. 07-03 (diamonds) comprised of 75.0 wt % polyorthoester, ropivacaine (4.75 wt % free base, 0.25 wt % HCl salt), 25.0 wt % N-methyl-2-pyrrolidone (NMP); Formulation No. 07-04 (squares) comprised of 56.4 wt % polyorthoester, 20.70 wt % ropivacaine free base, 22.9 wt % dimethyl acetamide (DMAc); Formulation No. 07-05 (circles) comprised of 45.0 wt % polyorthoester, 10.00 wt % ropivacaine free base, 45.0 wt % N-methyl-2-pyrrolidone; and Formulation No. 07-06 (triangles) comprised of 71.0 wt % polyorthoester, ropivacaine (4.50 wt % free base, 0.50 wt % HCl salt), and 24.0 wt % N-methyl-2-pyrrolidone.

Additional in vivo studies were conducted to further evaluate the release of additional exemplary active agents from delivery systems comprised of a polyorthoester and an aprotic solvent, using N-methylpyrrolidone and dimethyl acetamide as the exemplary solvents. Details of the studies are provided in Examples 9 and 12, respectively. In considering the study described in Example 9, the following compositions were administered: Formulation No. 07-03 comprised 75.0 wt % polyorthoester, ropivacaine (4.75 wt % free base, 0.25 wt % HCl salt), and 25.0 wt % N-methyl-2-pyrrolidone (NMP); Formulation No. 07-04 comprised 56.4 wt % polyorthoester, 20.70 wt % ropivacaine free base, 22.9 wt % dimethyl acetamide (DMAc); Formulation No. 07-05 comprised 45.0 wt % polyorthoester, 10.00 wt % ropivacaine free base, and 45.0 wt % N-methyl-2-pyrrolidone; and Formulation No. 07-06 comprised 71.0 wt % polyorthoester, ropivacaine (4.50 wt % free base, 0.50 wt % HCl salt), and 24.0 wt % N-methyl-2-pyrrolidone. Plasma samples were taken from each dog in the study 24 hours prior to administration, and after administration at the following time points: 1, 6, 12, 24, 48, 72, 96, 120, 144, and 168 hours. The plasma concentration of the active agent in the delivery systems, ropicavaine, as a function of time, in hours, is shown in FIG. 6. Advantageously, all formulations provided measurable plasma concentrations of ropivacaine for at least 5 days. The delivery systems administered contained from 45-75 wt % polyorthoester, from about 5-21 wt % ropivacaine (including both free base and acid salt forms), and from about 23-45 wt % aprotic solvent. In some instances, a small amount of a salt form of the active agent such as the hydrochloride salt, was included in the formulation to aid in dissolution. Interestingly, the formulations with the lowest weight percentage of ropivacaine, Formulations 07-03 (5 wt % total) and 07-06 (5 wt % total), exhibited higher Cmax values than did the formulations containing greater amounts of drug (10 wt % and 20 wt %). Both formulations 07-03 and 07-06 contained similar amounts of the aprotic solvent, NMP (25 wt % and 24 wt % respectively). This example further demonstrates the utility of delivery systems as described generally herein, to provide release into the bloodstream of an active agent over an extended period of time post administration.

Figure 7:
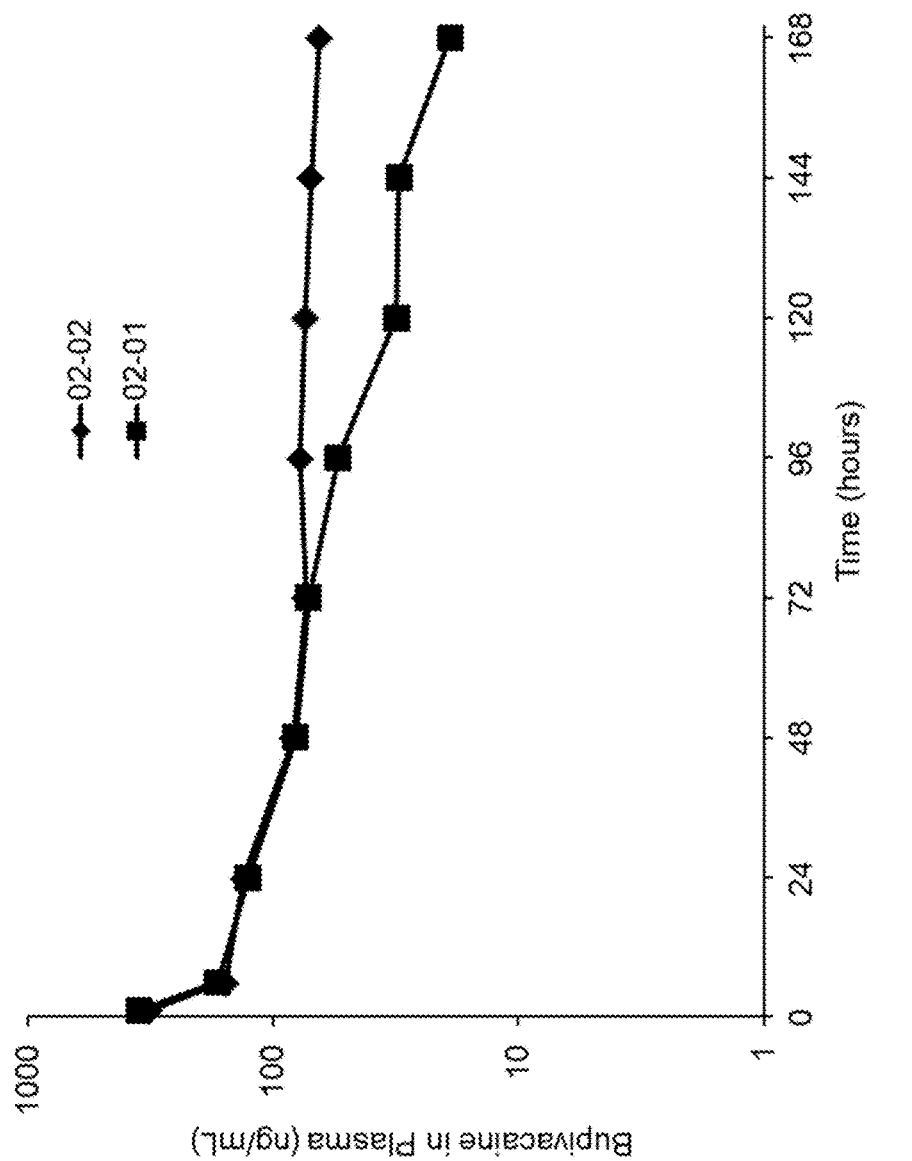
FIG. 7 is a graph of plasma concentration of bupivacaine, in ng/mL, in dogs, as a function of time, in hours, for two exemplary delivery systems comprising a polyorthoester, bupivacaine, and an aprotic solvent as described in Example 12. Data is shown for Formulation No. 02-01 comprised of 55.0 wt % polyorthoester, 15.0 wt % bupivacaine, and 30.0 wt % N-methyl-2-pyrrolidone (NMP); and for Formulation No. 02-02 comprised of 42.5 wt % polyorthoester, 15.0 wt % bupivacaine, and 42.5 wt % N-methyl-2-pyrrolidone.

A similar in vivo study is described in detail in Example 12, where the active agent comprised in the delivery systems was bupivacaine and the exemplary solvent was NMP. Two different formulations were administered as follows: 55.0 wt % polyorthoester, 15.0 wt % bupivacaine, and 30.0 wt % N-methyl-2-pyrrolidone (NMP) (Formulation 02-01); and 42.5 wt % polyorthoester, 15.0 wt % bupivacaine, and 42.5 wt % N-methyl-2-pyrrolidone (Formulation 02-02). Both formulations comprised the same weight percentage of drug, bupivacaine. A graph of plasma concentration of bupivacaine, in ng/mL, in dogs, as a function of time, in hours, is provided as FIG. 7. As can be seen, both formulations were effective to provide measurable plasma concentrations of bupivacaine for at least 5 days post-administration. Both formulations possessed similar Cmax values, however, the formulation containing a higher amount of NMP (42.5 wt %) was effective to maintain higher plasma concentrations of drug over the time period from about 4 days to about 7 days post-administration when compared to the formulation containing the lower amount of NMP (30 wt %).

A study was also conducted to examine the pharmacodynamics of local anesthetic formulations administered in vivo. Thus, in a further embodiment, formulations as provided herein are useful in reducing pain, e.g., in reducing post-surgical incisional pain in a patient. Turning back to the study carried out, as described in Example 13, two polyorthoester-aprotic solvent-anesthetic formulations were evaluated for their ability to reduce post-surgical incisional pain in a model system, i.e., a porcine model. The formulations administered locally comprised (i) 30.0 wt % NMP, 55.0 wt % polyorthoester of formula III, and 15 wt % bupivacaine; and (ii) 24.0 wt % NMP, 72.0 wt % polyorthoester, and 5.00 wt % ropivacaine. Administration was either by direct instillation or by injection into the tissue surrounding the wound. Activity of the anesthetic was evaluated by assessment of reduction of post-operative pain. Direct instillation of both formulations generally resulted in a greater degree of pain reduction in comparison to the injected formulations, with efficacy indicated up to at least six days post-administration. While the instilled samples were effective in reducing/eliminating pain shortly after administration, e.g., at the 1 hour time point, the injected samples were generally most effective in reducing pain at about 3-5 hours post-administration. All formulations, regardless of mode of administration, and for both anesthetics, were effective to reduce pain for up to at least 6 days post administration, and beyond. Thus, compositions such as provided herein are effective in providing extended pain relief, among other uses.

III. Aspects and Embodiments

Aspects and embodiments of the delivery systems, compositions, and related methods as provided herein are set forth below.

In a first aspect, provided herein is a delivery system, comprising: a polyorthoester; an aprotic solvent in which the polyorthoester is miscible to form a single phase; and a therapeutically active agent dispersed or solubilized in the single phase; wherein the active agent is released from the system over a period of between approximately 1 day and approximately 8 weeks.

In a second aspect, provided is a flowable composition, comprising: a polyorthoester; a solvent in which the polyorthoester is miscible to form a single phase; and a therapeutically active agent dispersed or solubilized in the single phase; wherein the solvent is an aprotic solvent with a dipole moment greater than about 2 Debye (D).

In a third aspect, provided herein is a method of treatment, comprising dispensing from a needle a composition comprised of a polyorthoester, an aprotic solvent in which the polyorthoester is miscible to form a single phase; and a therapeutically active agent dispersed or solubilized in the single phase, wherein the solvent is selected to achieve a controlled release of the active agent from the composition according to a predetermined release profile, and wherein the release of the active agent is for a period of between approximately 1 day and approximately 8 weeks.

In a first embodiment related to the delivery system of the first aspect or the flowable composition of the second aspect or the composition of the third aspect, the delivery system or flowable composition or composition has a viscosity of less than about 10,000 cP at 37° C.

In a second embodiment related to the first, second or third aspects above, the aprotic solvent is an organic solvent having a water solubility of greater than 25% by weight of the solvent in water at room temperature.

In a third embodiment related to the first, second or third aspects above, the aprotic solvent is a dipolar aprotic solvent.

In a fourth embodiment related to the first, second or third aspects above, the aprotic solvent is in a class selected from the group consisting of an amide, a biocompatible oil, an ester of an acid, an ester of an alcohol, an ether, a ketone, a sulfoxide, a triglyceride, and an ester of a triglyceride.

In a fifth embodiment related to the first, second or third aspects above, the aprotic solvent is an amide. In yet a further embodiment of the foregoing, the solvent is an amide selected from the group consisting of 2-pyrrolidone, dimethyl formamide, n-methyl-2-pyrrolidone, n-ethyl-2-pyrrolidone, dimethyl acetamide, n-cyclohexyl-2-pyrrolidone and caprolactam. In yet a further embodiment, the solvent is 1-dodecylazacycloheptan-2-one (azone).

In a sixth embodiment related to the first, second or third aspects above, the aprotic solvent is a biocompatible oil. In a further embodiment related to the foregoing, the solvent is a biocompatible oil, excluding non-hydrogenated vegetable oils, partially-hydrogenated vegetable oils, peanut oil, sesame oil or sunflower oil.

In a $7^{th}$ embodiment related to the first, second or third aspects above, the aprotic solvent is an ester of an acid. In a further embodiment related to the foregoing, the solvent is an ester of an acid selected from the group consisting of carboxylic acid esters and fatty acid esters, excluding propylene glycol dicaprate and propylene glycol dicaprylate. In yet a further embodiment related to the $7^{th}$ embodiment, the solvent is selected from the group consisting of ethyl acetate, benzyl benzoate, methyl acetate, isopropyl myristate, ethyl oleate, methyl lactate and ethyl lactate.

In an $8^{th}$ embodiment related to the first, second or third aspects above, the aprotic solvent is an ester of an alcohol. In an embodiment related to the foregoing, the solvent is propylene carbonate (4-methyl-1,3-diololan-2-one).

In a $9^{th}$ embodiment related to the first, second or third aspects above, the aprotic solvent is an ether. In an embodiment related to the foregoing, the ether is selected from dimethyl isosorbide and tetrahydrofuran.

In a $10^{th}$ embodiment related to the first, second or third aspects above, the aprotic solvent is a ketone. In yet a further embodiment related to the foregoing, the solvent is a ketone selected from the group consisting of acetone and methyl ethyl ketone. In yet another embodiment related to the $10^{th}$ embodiment, the solvent is a lactone selected from caprolactone and butyrolactone.

In an $11^{th}$ embodiment related to the first, second or third aspects above, the aprotic solvent is a sulfoxide. In a further embodiment related to the foregoing, the solvent is a sulfoxide selected from the group consisting of dimethyl sulfoxide and decylmethylsulfoxide. In a $12^{th}$ embodiment related to the first, second or third aspects above, the aprotic solvent is a triglyceride or an ester of a triglyceride.

In a $13^{th}$ embodiment related to the first, second or third aspects above, the solvent is not propylene glycol dicaprate, propylene glycol dicaprylate, glycofurol, a non- or partially-hydrogenated vegetable oil, glyceryl caprylate, glyceryl captate, glyceryl caprylate/caprate, glyceryl 10 caprylate/caprate/laurate, poly(ethylene glycol-copolypropylene glycol, poly(ethylene glycol)monomethyl ether 550, poly(ethylene glycol)dimethyl ether 250, glycerine triacetate, or a triglyceride.

In a $14^{th}$ embodiment related to the first, second or third aspects above, the aprotic solvent is 2-pyrrolidone.

In a 15th embodiment related to the first, second or third aspects above, the aprotic solvent is dimethylformamide.

In a 16th embodiment related to the first, second or third aspects above, the aprotic solvent is N-methyl-2-pyrrolidone.

In a 17th embodiment related to the first, second or third aspects above, the aprotic solvent is N-ethyl-2-pyrrolidone.

In an 18th embodiment related to the first, second or third aspects above, the aprotic solvent is dimethylacetamide.

In a 19th embodiment related to the first, second or third aspects above, the aprotic solvent is N-cyclohexyl-2-pyrrolidone.

In a 20th embodiment related to the first, second or third aspects above, the aprotic solvent is caprolactam.

In a 21st embodiment related to the first, second or third aspects above, the aprotic solvent is 1-dodecylazacycloheptan-2-one (azone).

In a 22nd embodiment related to the first, second or third aspects above, the aprotic solvent is ethyl acetate.

In a 23rd embodiment related to the first, second or third aspects above, the aprotic solvent is benzyl benzoate.

In a 24th embodiment related to the first, second or third aspects above, the aprotic solvent is methyl acetate.

In a 25th embodiment related to the first, second or third aspects above, the aprotic solvent is isopropyl myristate.

In a 26th embodiment related to the first, second or third aspects above, the aprotic solvent is ethyl oleate.

In a 27th embodiment related to the first, second or third aspects above, the aprotic solvent is methyl lactate.

In a 28th embodiment related to the first, second or third aspects above, the aprotic solvent is ethyl lactate.

In a 29th embodiment related to the first, second or third aspects above, the aprotic solvent is propylene carbonate (4-methyl-1,3-diololan-2-one).

In a 30th embodiment related to the first, second or third aspects above, the aprotic solvent is dimethyl ether.

In a 31st embodiment related to the first, second or third aspects above, the aprotic solvent is dimethyl isosorbide.

In a 32nd embodiment related to the first, second or third aspects above, the aprotic solvent is tetrahydrofuran.

In a 33rd embodiment related to the first, second or third aspects above, the aprotic solvent is acetone.

In a 34th embodiment related to the first, second or third aspects above, the aprotic solvent is methyl ethyl ketone.

In a 35th embodiment related to the first, second or third aspects above, the aprotic solvent is aprolactone.

In a 36th embodiment related to the first, second or third aspects above, the aprotic solvent is butyrolactone.

In a 37th embodiment related to the first, second or third aspects above, the aprotic solvent is dimethyl sulfoxide.

In a 38th embodiment related to the first, second or third aspects above, the aprotic solvent is decylmethylsulfoxide.

In a 39th embodiment related to the first, second or third aspects above, and any one of embodiments 1-38, the aprotic solvent is present in an amount ranging from about 10 percent to about 70 percent by weight, relative to the total weight of the composition.

In a 40th embodiment related to the first, second or third aspects above, or any one of embodiments 1-38, the aprotic solvent is present in the composition in an amount ranging from about 20 percent to about 50 percent by weight.

In a 41st embodiment related to the first, second or third aspects above, or any one of embodiments 1-38, the aprotic solvent is present in the composition in an amount ranging from about 10-60 wt %.

In a 42nd embodiment related to the first, second or third aspects above, or any one of embodiments 1-38, the aprotic solvent is present in the composition in an amount ranging from about 15-60 wt %.

In a 43rd embodiment related to the first, second or third aspects above, or any one of embodiments 1-38, the aprotic solvent is present in the composition in an amount ranging from about 15-50 wt %.

In a 44th embodiment related to the first, second or third aspects above, or any one of embodiments 1-38, the aprotic solvent is present in the composition in an amount ranging from about 20-60 wt %.

In a 45th embodiment related to the first, second or third aspects above, or any one of embodiments 1-38, the aprotic solvent is present in the composition in an amount ranging from about 25-50 wt %.

In a 46th embodiment related to the first, second or third aspects above, or any one of embodiments 1-38, the aprotic solvent is present in the composition in an amount ranging from about 30-70 wt %.

In a $47^{th(i)}$ embodiment related to the first, second or third aspects above, or any one of embodiments 1-38, the aprotic solvent is present in the composition in an amount ranging from about 30-60 wt %.

In a $47^{th(ii)}$ embodiment related to the first, second or third aspects above, or any one of embodiments 1-38, the aprotic solvent is present in the composition in an amount ranging from about 10-20 wt %.

In a $48^{th(i)}$ embodiment related to the first, second or third aspects above, or any one of embodiments 1-38, the aprotic solvent is present in the composition in an amount ranging from about 30-50 wt %.

In a $48^{th(ii)}$ embodiment related to the first, second or third aspects above, or any one of embodiments 1-38, the aprotic solvent is present in the composition in an amount ranging from about 15-25 wt %.

In a $49^{th(i)}$ embodiment related to the first, second or third aspects above, or any one of embodiments 1-38, the aprotic solvent is present in the composition in an amount ranging from about 35-70 wt %.

In a $49^{th(ii)}$ embodiment related to the first, second or third aspects above, or any one of embodiments 1-38, the aprotic solvent is present in the composition in an amount ranging from about 20-30 wt %.

In a $50^{th(i)}$ embodiment related to the first, second or third aspects above, or any one of embodiments 1-38, the aprotic solvent is present in the composition in an amount ranging from about 35-60 wt %.

In a $50^{th(ii)}$ embodiment related to the first, second or third aspects above, or any one of embodiments 1-38, the aprotic solvent is present in the composition in an amount ranging from about 15-35 wt %.

In a $51^{st(i)}$ embodiment related to the first, second or third aspects above, or any one of embodiments 1-38, the aprotic solvent is present in the composition in an amount ranging from about 35-50 wt %.

In a $51^{st(ii)}$ embodiment related to the first, second or third aspects above, or any one of embodiments 1-38, the aprotic solvent is present in the composition in an amount ranging from about 20-35 wt %.

In a $51^{st(iii)}$ embodiment related to the first, second or third aspects above, or any one of embodiments 1-38, the aprotic solvent is present in the composition in an amount ranging from about 20-40 wt %.

In a 52nd embodiment related to the first, second or third aspects above, and any one of embodiments 1-51, the polyorthoester has a structure defined by formula I, formula II, formula III or formula IV:

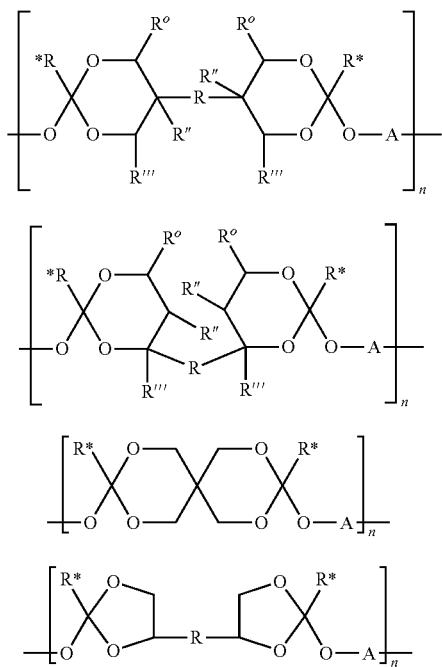

where:

R is a bond, —(CH$_2$)$_a$—, or —(CH$_2$)$_b$—O—(CH$_2$)$_c$—; where a is an integer of 1 to 10, and b and c are independently integers of 1 to 5; R* is a C$_{1-4}$ alkyl; R$^o$, R" and R'" are each independently H or C$_{1-4}$ alkyl; n is an integer of at least 5; and A is a diol.

In a 53$^{rd}$ embodiment related to the first, second or third aspects above, and any one of embodiments 1-51, the polyorthoester has a structure of formula III where R is a bond, —(CH$_2$)$_a$—, or —(CH$_2$)$_b$—O—(CH$_2$)$_n$—; where a is an integer of 1 to 10, and b and c are independently integers of 1 to 5; R* is a C$_{1-4}$ alkyl; R$^o$, R" and R'" are each independently H or C$_{1-4}$ alkyl; n is an integer of at least 5; and A is R$^1$, R$^2$, R$^3$, or R$^4$, where R$^1$ is:

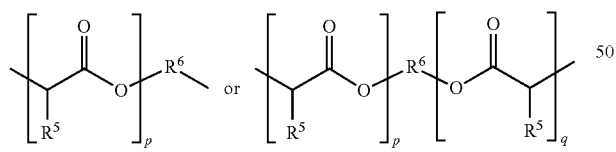

where p and q are integers that vary from between about 1 to 20 and the average number of p or the average of the sum of p and q is between 1 and 7 in an least a portion of the monomeric units of the polymer; R$^5$ is hydrogen or C$_{1-4}$ alkyl; and R$^6$ is:

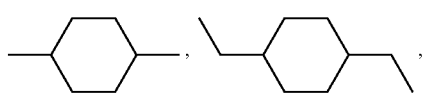

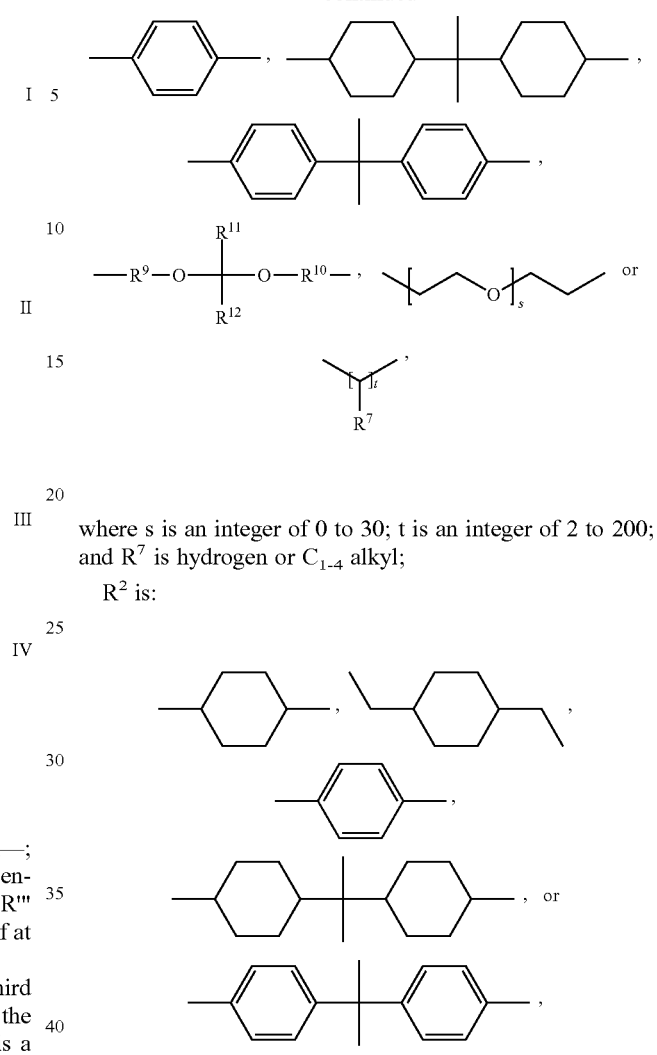

where s is an integer of 0 to 30; t is an integer of 2 to 200; and R$^7$ is hydrogen or C$_{1-4}$ alkyl;

R$^2$ is:

R$^3$ is:

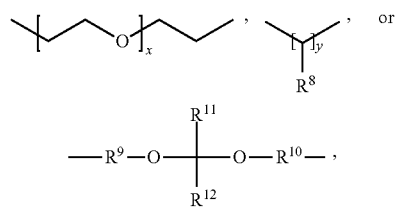

where x is an integer of 0 to 100; y is an integer of 2 to 200; R$^8$ is hydrogen or C$_{1-4}$ alkyl; R$^9$ and R$^{10}$ are independently C$_{1-12}$ alkylene; R$^{11}$ is hydrogen or C$_{1-6}$ alkyl and R$^{12}$ is C$_{1-6}$ alkyl; or R$^{11}$ and R$^{12}$ together are C$_{3-10}$ alkylene; and R$^4$ is the residue of a diol containing at least one functional group independently selected from amide, imide, urea, and urethane groups.

In a 54$^{th}$ embodiment related to the first, second or third aspects above, and any one of embodiments 1-51, the polyorthoester has a structure according to formula III where A is R$^1$, R$^3$, or R$^4$, where R$^1$ is:

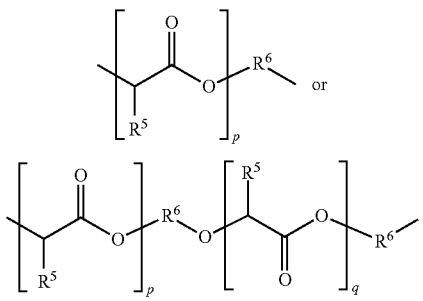

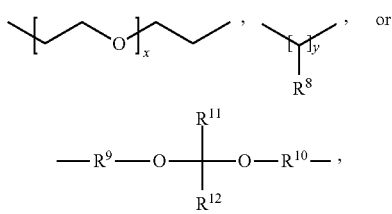

where p and q are integers that vary from between about 1 to 20 and the average number of p or the average of the sum of p and q is between 1 and 7 in an least a portion of the monomeric units of the polymer; $R^3$ and $R^6$ are each independently:

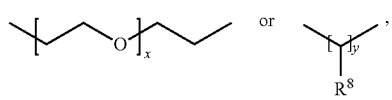

where x is an integer of 0 to 30; y is an integer of 2 to 200; $R^8$ is hydrogen or $C_{1-4}$ alkyl; $R^9$ and $R^{10}$ are independently $C_{1-12}$ alkylene; $R^{11}$ is hydrogen or $C_{1-6}$ alkyl and $R^{12}$ is $C_{1-6}$ alkyl; or $R^{11}$ and $R^{12}$ together are $C_{3-10}$ alkylene; $R^4$ is a residual of a diol containing at least one functional group independently selected from amide, imide, urea and urethane groups; and $R^5$ is hydrogen or $C_{1-4}$ alkyl.

In a 55$^{th}$ embodiment related to the first, second or third aspects above, and any one of embodiments 1-53, the polyorthoester has a molecular weight between 3,000 and 10,000.

In a 56$^{th(i)}$ embodiment related to embodiments 52-54, the fraction of the A units that are of the formula $R^1$ is between 0 and 25 mole percent. In a 56$^{th(II)}$ embodiment related to embodiments 52-54, the fraction of the A units that are of the formula $R^1$ is between 0 and 10 mole percent. In a 56$^{th(iii)}$ embodiment related to embodiments 52-54, the fraction of the A units that are of the formula $R^1$ is between 0 and 5 mole percent. In a 56$^{th(iv)}$ embodiment related to embodiments 52-54, the fraction of the A units that are of the formula $R^1$ is between 10 and 25 mole percent.

In a 57$^{th}$ embodiment related to embodiments 52-54, the polyorthoester is of formula III, where none of the units have A equal to $R^2$; $R^3$ is:

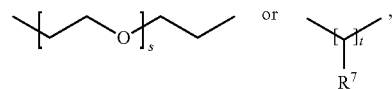

where x is an integer of 0 to 10; y is an integer of 2 to 30; and $R^6$ is:

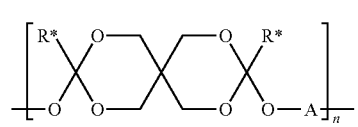

where s is an integer of 0 to 10; t is an integer of 2 to 30; and $R^5$, $R^7$, and $R^8$ are independently hydrogen or methyl. In yet another embodiment related to embodiment 57, $R^3$ and $R^6$ are both $-(CH_2-CH_2-O)_2-(CH_2-CH_2)-$; $R^5$ is methyl; and p is 1 or 2.

In a 58$^{th}$ embodiment related to the first, second or third aspects above, and any one of embodiments 1-51, the polyorthoester is selected from formulas III and IV below:

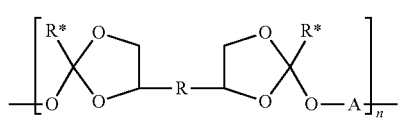

where R is a bond, $-(CH_2)_a-$, or $-(CH_2)_bO(CH_2)_c-$; where a is an integer from 1 to 10, and b and c are independently integers from 1-5; R* is a $C_{1-4}$ alkyl; R0, RII and RIII are each independently H or $C_{1-4}$ alkyl; n is an integer of at least 5, for example, from 5 to 1000; and A is $R^1$, $R^2$, $R^3$, or $R^4$, where $R^1$ is

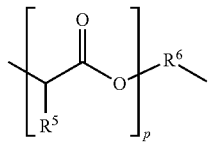

where: p is an integer of 1 to 20; $R^5$ is hydrogen or C1-4 alkyl; and
$R^6$ is:

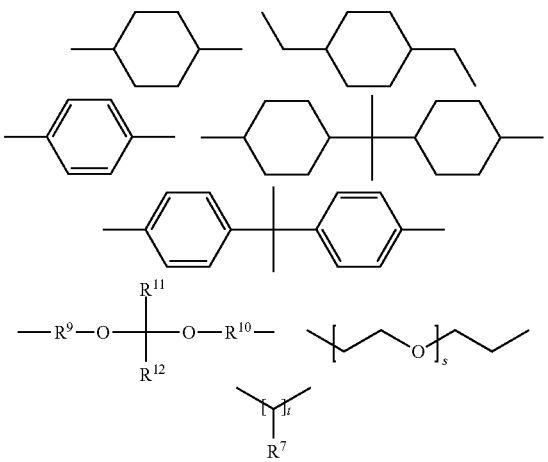

where:
s is an integer of 0 to 30; t is an integer of 2 to 200; and $R^7$ is hydrogen or $C_{1-4}$ alkyl;
$R^2$ is:

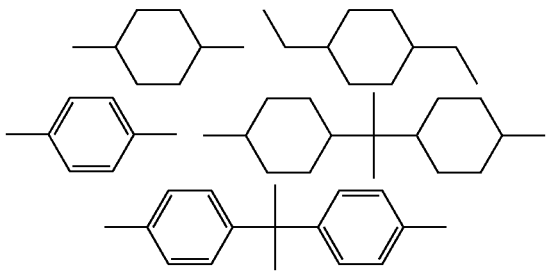

$R^3$ is:

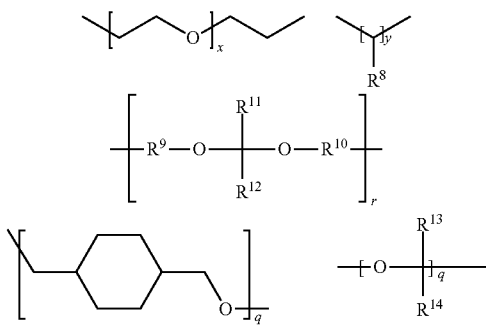

where:
x is an integer of 0 to 100; y is an integer of 2 to 200;
q is an integer of 2 to 20; r is an integer of 1 to 20; $R^8$ is hydrogen or C1-4 alkyl;
$R^9$ and $R^{19}$ are independently $C_{1-12}$ alkylene; $R^{11}$ is hydrogen or C1-6 alkyl and $R^{12}$ is C1-6 alkyl; or $R^{11}$ and $R^{12}$ together are $C_{3-10}$ alkylene; and
$R^4$ is the residue of a diol containing at least one functional group independently selected form amide, imide, urea, and urethane groups;
in which at least 0.01 mol percent of the A units are of the formula $R^1$. In a sub-embodiment of the 58th embodiment above, none of the A units are of formula $R^1$.

In a 59th embodiment related to the first, second or third aspects above, or any one of embodiments 1-58, the amount of polyorthoester ranges from about 30 percent to about 90 percent by weight relative to the overall composition or delivery system.

In a 60th embodiment related to the first, second or third aspects above, or any one of embodiments 1-58, the amount of polyorthoester ranges from about 50 percent to about 80 percent by weight relative to the overall composition or delivery system.

In a 61st embodiment related to the first, second or third aspects above, or any one of embodiments 1-60, the active agent is dissolved in the composition or delivery system.

In a 62nd embodiment related to the first, second or third aspects above, or any one of embodiments 1-60, the active agent is dispersed in the composition or delivery system.

In a 63rd embodiment related to the first, second or third aspects above, or any one of embodiments 1-60, the amount active agent in the composition or delivery system ranges from about 1 wt % to 20 wt %.

In a 64th embodiment related to the first, second or third aspects above, or any one of embodiments 1-60, the amount active agent in the composition or delivery system ranges from about 10 wt % to 20 wt %.

In a 65th embodiment related to the first, second or third aspects above, or any one of embodiments 1-60, the amount active agent in the composition or delivery system ranges from about 2 wt % to 5 wt %.

In a 66th embodiment related to the first, second or third aspects above, or any one of embodiments 1-60, the amount active agent in the composition or delivery system ranges from about 10 wt % to 15 wt %.

In a 67th embodiment related to the first, second or third aspects above, or any one of embodiments 1-60, the amount active agent in the composition or delivery system ranges from about 15 wt % to 20 wt %.

In a 68th embodiment related to the first, second or third aspects above, or any one of embodiments 1-60, the amount active agent in the composition or delivery system is about 1 wt %.

In a 69th embodiment related to the first, second or third aspects above, or any one of embodiments 1-60, the amount active agent in the composition or delivery system is about 2 wt %.

In a 70th embodiment related to the first, second or third aspects above, or any one of embodiments 1-60, the amount active agent in the composition or delivery system is about 3 wt %.

In a 71st embodiment related to the first, second or third aspects above, or any one of embodiments 1-60, the amount active agent in the composition or delivery system is about 4 wt %.

In a 72nd embodiment related to the first, second or third aspects above, or any one of embodiments 1-60, the amount active agent in the composition or delivery system is about 5 wt %.

In a 73rd embodiment related to the first, second or third aspects above, or any one of embodiments 1-60, the amount active agent in the composition or delivery system is about 6 wt %.

In a 74th embodiment related to the first, second or third aspects above, or any one of embodiments 1-60, the amount active agent in the composition or delivery system is about 7 wt %.

In a 75th embodiment related to the first, second or third aspects above, or any one of embodiments 1-60, the amount active agent in the composition or delivery system is about 8 wt %.

In a 76th embodiment related to the first, second or third aspects above, or any one of embodiments 1-60, the amount active agent in the composition or delivery system is about 9 wt %.

In a 77th embodiment related to the first, second or third aspects above, or any one of embodiments 1-60, the amount active agent in the composition or delivery system is about 10 wt %.

In a 78th embodiment related to the first, second or third aspects above, or any one of embodiments 1-60, the amount active agent in the composition or delivery system is about 11 wt %.

In a 79th embodiment related to the first, second or third aspects above, or any one of embodiments 1-60, the amount active agent in the composition or delivery system is about 12 wt %.

In a 80th embodiment related to the first, second or third aspects above, or any one of embodiments 1-60, the amount active agent in the composition or delivery system is about 13 wt %.

In a 81st embodiment related to the first, second or third aspects above, or any one of embodiments 1-60, the amount active agent in the composition or delivery system is about 14 wt %.

In a 82nd embodiment related to the first, second or third aspects above, or any one of embodiments 1-60, the amount active agent in the composition or delivery system is about 15 wt %.

In a 83rd embodiment related to the first, second or third aspects above, or any one of embodiments 1-60, the amount active agent in the composition or delivery system is about 16 wt %.

In a 84th embodiment related to the first, second or third aspects above, or any one of embodiments 1-60, the amount active agent in the composition or delivery system is about 17 wt %.

In a 85th embodiment related to the first, second or third aspects above, or any one of embodiments 1-60, the amount active agent in the composition or delivery system is about 18 wt %.

In a 86th embodiment related to the first, second or third aspects above, or any one of embodiments 1-60, the amount active agent in the composition or delivery system is about 19 wt %.

In a 87th embodiment related to the first, second or third aspects above, or any one of embodiments 1-60, the amount active agent in the composition or delivery system is about 20 wt %.

In an 88th embodiment related to the first, second or third aspects above, or any of embodiments 1-87, the active agent in the composition or delivery system is granisetron.

In an 89th embodiment related to the first, second or third aspects above, or any of embodiments 1-87, the active agent in the composition or delivery system is a local "caine"-type anesthetic.

In a 90th embodiment related to the first, second or third aspects above, or any of embodiments 1-87, the active agent in the composition or delivery system is selected from bupivacaine, levobupivacaine, dibucaine, mepivacaine, procaine, lidocaine, tetracaine, and ropivacaine.

In a 91st embodiment related to the first, second or third aspects above, or any of embodiments 1-87, the active agent in the composition or delivery system is bupivacaine.

In an 92nd embodiment related to the first, second or third aspects above, or any of embodiments 1-87, the active agent in the composition or delivery system is ropivacaine.

In an 93rd embodiment related to the first, second or third aspects above, or any of embodiments 1-87, the active agent in the composition or delivery system is levobupivacaine.

In an 94th embodiment related to the first, second or third aspects above, or any of embodiments 1-87, the active agent in the composition or delivery system is dibucaine.

In an 95th embodiment related to the first, second or third aspects above, or any of embodiments 1-87, the active agent in the composition or delivery system is mepivacaine.

In an 96th embodiment related to the first, second or third aspects above, or any of embodiments 1-87, the active agent in the composition or delivery system is procaine.

In an 97th embodiment related to the first, second or third aspects above, or any of embodiments 1-87, the active agent in the composition or delivery system is lidocaine.

In an 98th embodiment related to the first, second or third aspects above, or any of embodiments 1-87, the active agent in the composition or delivery system is tetracaine.

In an 99th embodiment related to the first, second or third aspects above, or any of embodiments 1-87, the active agent in the composition or delivery system is an anti-emetic.

In a 100th embodiment related to the first, second or third aspects above, the polyorthoester is represented by the structure shown as Formula III, the active agent is granisetron in an amount between 1-5 percent by weight, and the aprotic solvent is DMSO in an amount between 10-35 percent by weight.

In an 101st embodiment related to the first, second or third aspects above, or any of embodiments 1-100, the composition or delivery system has a viscosity of less than about 10,000 cP at 37° C.

In a 102nd embodiment related to the first, second or third aspects above, or any of embodiments 1-87, the active agent in the composition is an opioid.

In a 103rd embodiment related to the first, second or third aspects above, or any of embodiments 1-87, the active agent in the composition is bupenorphine.

In a fourth aspect, provided is method of administering a therapeutically active agent comprising dispensing from a needle a delivery system or a composition related to the first or second or aspects above, or any one of embodiments 1-103.

IV. Examples

The following examples are illustrative in nature and are in no way intended to be limiting.

Example 1

Delivery Systems Comprising an Aprotic Solvent

Compositions, 2 to 5 grams of each, of a polyorthoester of formula III with triethylene glycol and $R^1$ in a 2:1 ratio, granisetron base and varying amounts of DMSO or DMAC were prepared by dissolving the appropriate amount of granisetron base into each solvent at approximately 80° C.

The drug solutions were then mixed with the appropriate amount of polymer at an elevated temperature, until homogenous, to form compositions with 20% (DMAC only), 30%, 40%, and 50% solvent and 2% granisetron base. The release of solvent from each composition was determined by placing a small amount of each polymer formulation (approximately 50 mg) into 15-20 mL of phosphate buffered saline in glass scintillation vials. The samples were then incubated at 37° C. without agitation. At 24 hour intervals the vials were inverted several times and aliquots of the buffer solution were removed and analyzed for each solvent by gas chromatography. The results are shown in FIGS. 1A-1B and in the tables below.

TABLE 1-1

In Vitro Release of DMSO

| | Percent Solvent Released for Compositions with Indicated Amount of DMSO | | |
|---|---|---|---|
| Time (hours) | 30% DMSO | 40% DMSO | 50% DMSO |
| 0 | 0% | 0% | 0% |
| 24 | 30.1% | 43.5% | 58.5% |
| 48 | 40.9% | 57.0% | 71.7% |
| 72 | 73.1% | 70.0% | 83.7% |

TABLE 1-1-continued

In Vitro Release of DMSO

Percent Solvent Released for Compositions with Indicated Amount of DMSO

| Time (hours) | 30% DMSO | 40% DMSO | 50% DMSO |
|---|---|---|---|
| 96 | 87.0% | 87.1% | 93.0% |
| 168 | 90.4% | 94.9% | 94.3% |

TABLE 1-2

In Vitro Release of DMAC

Percent Solvent Released for Compositions with Indicated Amount of DMAC

| Time (hours) | 20% DMAC | 30% DMAC | 40% DMAC | 50% DMAC |
|---|---|---|---|---|
| 0 | 0% | 0% | 0% | 0% |
| 24 | 78.9% | 92.1% | 90.0% | 112.4% |
| 48 | 82.1% | 105.6% | 88.1% | 101.0% |
| 72 | 98.8% | 100.3% | 97.1% | 98.7% |
| 96 | 97.3% | 97.7% | 95.7% | 96.3% |
| 168 | 107.3% | 109.2% | 107.0% | 107.0% |

Example 2

Measurement of Viscosity

Compositions, 2 to 5 grams of each, of a polyorthoester (POE) of formula III, granisetron base and varying amounts of dimethyl sulfoxide or N-methylpyrrolidone were prepared by dissolving the appropriate amount of granisetron base into each solvent at approximately 80° C. The drug solutions were then mixed with the appropriate amount of polymer at an elevated temperature, until homogenous, to form compositions with 10%, 20%, and 30% solvent and 2% granisetron base. Viscosity of the compositions was measured using a Brookfield cone and plate viscometer. The viscosity measurements are performed at 37° C.

TABLE 2-1

Viscosity of Compositions

| | Viscosity in DMSO (cP) | Viscosity in NMP (cP) |
|---|---|---|
| 90% POE/10% Solvent | 199,630 | 117,663 |
| 80% POE/20% Solvent | 14,162 | 9966 |
| 70% POE/30% Solvent | 2608 | 1633 |

Example 3

Drug Release Modulated by Selection of Aprotic Solvent

Compositions, 2 to 5 grams of each, of a polyorthoester of Formula III, granisetron, and varying amounts of DMSO or DMAC were prepared dissolving the appropriate amount of granisetron base into each solvent at approximately 80° C. The drug solutions were then mixed with the appropriate amount of polymer at an elevated temperature, until homogenous, to form compositions with 20% (DMAC only), 30%, 40%, and 50% solvent and 2% granisetron base. The release of solvent from each composition was determined by placing a small amount of each polymer formulation (approximately 50 mg) into 15-20 mL of phosphate buffered saline in glass scintillation vials. The samples were then incubated at 37° C. without agitation. At 24 hour intervals the vials were inverted several times and aliquots of the buffer solution were removed and analyzed for granisetron by high performance liquid chromatography. The results are shown in FIGS. 2A-2B and in the tables below.

TABLE 3-1

In Vitro Release of Granisetron from Composition with DMSO

| | Granisetron Release (%) | | |
|---|---|---|---|
| Time (hrs) | 30% DMSO | 40% DMSO | 50% DMSO |
| 0 | 0% | 0% | 0% |
| 24 | 28.2% | 44.8% | 62.0% |
| 48 | 36.9% | 52.9% | 71.3% |
| 72 | 66.2% | 64.2% | 84.0% |
| 96 | 73.9% | 71.2% | 93.1% |
| 168 | 96.1% | 100.7% | 101.5% |

TABLE 3-2

In Vitro Release of Granisetron from Composition with DMAC

| | Granisetron Release (%) | | | |
|---|---|---|---|---|
| Time (hrs) | 20% DMAC | 30% DMAC | 40% DMAC | 50% DMAC |
| 0 | 0% | 0% | 0% | 0% |
| 24 | 30.9% | 41.0% | 40.4% | 71.3% |
| 48 | 47.3% | 100.0% | 51.1% | 80.8% |
| 72 | 98.4% | 103.6% | 81.2% | 94.8% |
| 96 | 110.2% | 115.0% | 90.5% | 104.9% |
| 168 | 106.9% | 106.5% | 101.4% | 103.9% |

Example 4

Delivery Systems Comprising an Aprotic Ether Solvent

Compositions of a polyorthoester of formula III, granisetron base and two concentrations of dimethyl isosorbide were prepared by first dissolving the appropriate amount of granisetron base into dimethyl isosorbide at elevated temperature. The drug solution was then mixed with the appropriate amount of polymer at an elevated temperature, until homogenous, to form compositions with 19.6% and 9.8% dimethyl isosorbide and 2% granisetron base. The release of drug from each composition was determined by placing a small amount of each polymer formulation (approximately 50 mg) into 15-20 mL of phosphate buffered saline in glass scintillation vials. The samples were then incubated at 37° C. without agitation. At 24 hour intervals the vials were inverted several times and aliquots of the buffer solution were removed and analyzed for granisetron by high performance liquid chromatography. The results are shown in FIG. 4 and in the Table 4-1 below.

TABLE 4-1

In Vitro Release of Granisetron

| Time (hrs) | 19.6% Dimethyl isosorbide | 9.8% Dimethyl isosorbide |
|---|---|---|
| 2 | 4% | 4% |
| 4 | 7% | 6% |
| 6 | 10% | 9% |

TABLE 4-1-continued

In Vitro Release of Granisetron

| Time (hrs) | 19.6% Dimethyl isosorbide | 9.8% Dimethyl isosorbide |
|---|---|---|
| 24 | 27% | 27% |
| 48 | 36% | 37% |
| 72 | 60% | 45% |
| 96 | 84% | 73% |
| 168 | 88% | 110% |
| 192 | 88% | 110% |
| 216 | 88% | 111% |
| 240 | 89% | 111% |
| 264 | 89% | 111% |

Example 5

Delivery Systems Comprising an Aprotic Solvent

Compositions comprised of a polyorthoester of Formula III and the following drugs and solvents are prepared: meloxicam, granisetron, mepivacaine, bupivacaine, ropivacaine, and buprenorphine and DMSO, NMP, DMAC and dimethyl isosorbide. Release of drug and solvent from the compositions is measured in an in vitro dissolution apparatus. Rate of drug release correlates with rate of solvent release for DMSO and NMP. Compositions with DMAC provide a rate of drug release that depends on the solubility of the drug in the solvent.

Example 6

Pharmacokinetic Analysis of Granisetron Formulations in Canines

Ten dogs were treated with a formulation containing, 2% granisetron base in 63.7% polyorthoester of Formula III—34.3% DMSO (5 male-5 female) on day 1 of week 1. Each dog received the entire contents of 1 syringe containing 0.5 grams formulation (10 mg granisetron). Plasma samples were taken from each dog at the following time points: −24, 1, 6, 12, 24, 48, 72, 96, 120, 144, and 168 hours and frozen. On day 1 of week 3, the study was repeated in the same 10 dogs. For this second portion of the study, the ten dogs were treated with a formulation containing, 2% granisetron base in 71.5% polyorthoester of Formula III—26.5% DMSO (5 male, 5 female). Again, plasma samples were taken from each dog at the following time points: −24, 1, 6, 12, 24, 48, 72, 96, 120, 144, and 168 hours and frozen. The plasma samples were subsequently analyzed by LC/MS/MS for granisetron. A plot of the plasma concentration of granisetron versus time is presented in FIG. 5. Both formulations provided measurable plasma concentrations of granisetron for at least 5 days. The formulation with the higher amount of DMSO gave a higher Cmaxthan did the formulation with 26.5% DMSO.

Example 7

Ropivacaine Delivery Systems Comprising an Aprotic Solvent

Compositions containing between 45% to 80% polyorthoester of formula III, between 20% and 45% of an aprotic solvent, and between 4% and 22.0% ropivaciane were prepared. Ropivacaine used in these compositions optionally contained a combination of ropivacaine base and ropivacaine hydrochloride. For compositions where the ropivacaine was in solution, the composition was prepared by first the dissolving the appropriate amount of ropivacaine base into the appropriate amount of aprotic solvent at approximately 80° C. The drug solution was then mixed with the appropriate amount of polymer at an elevated temperature, until homogenous. For compositions where the ropivacaine was in suspension, the composition was prepared by first combining the appropriate amount of polyorthoester polymer and the appropriate amount of aprotic solvent at approximately 80° C. The solution was cooled to approximately room temperature and the ropivacaine was added to the polymer solvent mixture. Exemplary compositions are presented in Table 7-1.

TABLE 7-1

Ropivacaine Delivery Systems: Polyorthoester-Aprotic Solvent Compositions

| Formulation ID | Solvent ID | Ropivacaine Base % | Ropivacaine HCl Salt % | % POE | % Solvent | Ropivacaine Composition Form |
|---|---|---|---|---|---|---|
| 07-01 | DMAc | 22.00% | 0.00% | 53.7% | 24.2% | Suspension |
| 07-02 | NMP | 9.10% | 0.50% | 45.2% | 45.2% | Dissolved |
| 07-03 | NMP | 4.75% | 0.25% | 72.0% | 24.0% | Dissolved |
| 07-04 | DMAc | 20.70% | 0.00% | 56.4% | 22.9% | Suspension |
| 07-05 | NMP | 10.00% | 0.00% | 45.0% | 45.0% | Dissolved |
| 07-06 | NMP | 4.50% | 0.50% | 71.0% | 24.0% | Dissolved |
| 07-07 | NMP | 4.75% | 0.25% | 66.5% | 28.5% | Dissolved |
| 07-09 | NMP | 4.00% | 1.00% | 80.0% | 20.0% | Dissolved |
| 07-10 | NMP | 3.50% | 1.50% | 80.0% | 20.0% | Dissolved |
| 07-11 | DMSO NMP | 3.96% | 0.24% | 68.5% | 4.7% DMSO 22.5% NMP | Dissolved |
| 07-12 | NMP | 3.80% | .020% | 72.0% | 24.0% | Dissolved |
| 07-13 | DMSO | 9.00% | 0.00% | 49.7% | 41.3% | Dissolved |
| 07-14 | DMSO | 4.15% | 0.85% | 52.0% | 43.0% | Dissolved |
| 07-15 | NMP | 3.60% | 0.40% | 67.1% | 28.9% | Dissolved |
| 07-16 | NMP | 9.0% | 1.0% | 65.0% | 25.0% | Suspension |
| 07-17 | NMP | 7.5% | 2.5% | 65.0% | 25.0% | Suspension |
| 07-18 | NMP | 5.0% | 5.0% | 65.0% | 25.0% | Suspension |
| 07-19 | DMAc | 9.0% | 1.1% | 71.9% | 17.9% | Suspension |
| 07-20 | DMAc | 7.4% | 2.6% | 72.0% | 18.0% | Suspension |
| 07-21 | DMAc | 5.0% | 5.0% | 72.0% | 18.0% | Suspension |

Example 8

In-Vitro Release of Ropivacaine Compositions

The release of ropivacaine from the composition was determined by placing a small amount of the polymer formulation (approximately 50 mg) into 150 mL of phosphate buffered saline. The samples were then incubated at 37° C. without agitation. At 24 hour intervals, 1 mL samples were taken from the vials without any agitation of the solution. Each sample was analyzed by HPLC to determine the concentration of ropivacaine. The cumulative drug release from the 50 mg depot was then calculated.

TABLE 8-1

In Vitro Release of Ropivacaine

Percent Ropivacaine Released for Compositions

| Composition # | 24 hrs | 48 hrs | 72 hrs | 96 hrs | 120 hrs | 144 hrs | 168 hrs | 192 hrs | 216 hrs |
|---|---|---|---|---|---|---|---|---|---|
| 07-02 | 35.78 | 72.20 | 83.30 | 86.60 | 91.44 | 95.45 | N/S | N/S | N/S |
| 07-03 | 45.26 | 51.67 | 52.54 | 58.65 | 67.06 | 69.99 | N/S | N/S | N/S |
| 07-04 | 25.09 | 34.35 | 37.08 | 45.69 | 55.92 | 63.29 | N/S | N/S | N/S |
| 07-06 | 26.55 | 43.97 | 57.01 | 71.73 | N/S | N/S | 93.96 | 97.35 | |
| 07-08 | 29.28 | 50.98 | 63.79 | 79.06 | 112.86 | 121.67 | N/S | N/S | N/S |
| 07-11 | 8.61 | 18.02 | 25.49 | 34.17 | N/S | N/S | 59.53 | 81.58 | N/S |
| 07-13 | 10.03 | 29.17 | 39.27 | 58.08 | 67.97 | 77.05 | N/S | N/S | N/S |
| 07-14 | 20.66 | 45.77 | 48.48 | 61.73 | 76.75 | 80.08 | N/S | N/S | N/S |
| 07-15 | 31.80 | 40.73 | 50.54 | 54.33 | N/S | N/S | N/S | 85.13 | 89.20 |

N/S—not sampled

Example 9

Pharmacokinetic Analysis of Ropivacaine Formulations in Canines

In a series of pharmacokinetic studies, ten dogs (5 male-5 female) were treated with the formulations listed in Table 8-1. Dogs received the entire contents of 1 syringe containing sufficient polyorthoester formulation to deliver approximately 100 mg of ropivacaine. Plasma samples were taken from each dog at the following time points: −24, 1, 6, 12, 24, 48, 72, 96, 120, 144, and 168 hours and frozen. The plasma samples were subsequently analyzed by LC/MS/MS for ropivacaine. A plot of the plasma concentration of ropivacaine versus time is presented in FIG. 6. All formulations provided measurable plasma concentrations of ropivaicaine for at least 5 days.

TABLE 9-1

Ropivcacaine Formulations Used in PK Study in Canines

| Formulation ID | Solvent ID | Ropivacaine Base % | Ropivacaine HCl % | % POE | % Solvent | Ropivacaine Composition Form |
|---|---|---|---|---|---|---|
| 07-03 | NMP | 4.75% | 0.25% | 75.0% | 25.0% | Dissolved |
| 07-04 | DMAc | 20.70% | 0.00% | 56.4% | 22.9% | Suspension |
| 07-05 | NMP | 10.00% | 0.00% | 45.0% | 45.0% | Dissolved |
| 07-06 | NMP | 4.50% | 0.50% | 71.0% | 24.0% | Dissolved |

Example 10

Bupivacaine Delivery Systems Comprising an Aprotic Solvent

Compositions containing between approximately 42% to 60% polyorthoester of formula III, between approximately 30% and 42% of an aprotic solvent, and between approximately 9% and 15% bupivacaine base were prepared. The composition was prepared by first the dissolving the appropriate amount of bupivacaine base into the appropriate amount of aprotic solvent at approximately 80° C. The drug solution was then mixed with the appropriate amount of polymer at an elevated temperature, until homogenous. Exemplary compositions are presented in Table 10-1.

TABLE 10-1

Bupivacaine Delivery Systems: Polyorthoester-Aprotic Solvent Compositions

| Formulation ID | Solvent ID | % Drug | % POE | % Solvent |
|---|---|---|---|---|
| 02-01 | NMP | 15.0% | 55.0% | 30.0% |
| 02-01 | NMP | 15.0% | 55.0% | 30.0% |
| 02-02 | NMP | 15.0% | 42.5% | 42.5% |
| 02-03 | NMP | 9.5% | 60.3% | 30.2% |
| 02-04 | NMP | 9.9% | 59.3% | 30.7% |

Example 11

In-Vitro Release of Bupivacaine Compositions

The release of bupivacaine from the composition was determined by placing a small amount of the polymer formulation (approximately 50 mg) into 150 mL of phosphate buffered saline. The samples were then incubated at 37° C. without agitation. At 24 hour intervals, 1 mL samples were taken from the vials without any agitation of the solution. Each sample was analyzed by HPLC to determine the concentration of bupivacaine. The cumulative drug release from the 50 mg depot was then calculated.

TABLE 11-1

In Vitro Release of Bupivacaine

| Composition # | Percent Bupivacaine Released for Compositions | | | | | | |
|---|---|---|---|---|---|---|---|
| | 24 hrs | 48 hrs | 72 hrs | 96 hrs | 168 hrs | 192 hrs | 216 hrs |
| 02-01 | 34.38 | 41.24 | 47.86 | 53.05 | 67.50 | 72.14 | 80.94 |
| 02-03 | 19.66 | 24.54 | 31.49 | NS | 43.33 | 50.54 | N/S |

Example 12

Pharmacokinetic Analysis of Bupivacaine Formulations in Canines

In a series of pharmacokinetic studies, between 2 and 10 beagles were treated with the formulations listed in Table 12-1 (Example 10). Dogs received the entire contents of 1 syringe containing sufficient polyorthoester formulation to deliver approximately 100 mg of bupivacaine. Plasma samples were taken from each dog at the following time points: −24, 1, 6, 12, 24, 48, 72, 96, 120, 144, and 168 hours and frozen. The plasma samples were subsequently analyzed by LC/MS/MS for bupivacaine. A plot of the plasma concentration of bupivacaine versus time is presented in FIG. 7. All formulations provided measurable plasma concentrations of bupivacaine for at least 5 days.

TABLE 12-1

Bupivacaine Formulations Used in PK Study in Canines

| Formulation ID | Solvent ID | % Drug | % POE | % Solvent |
|---|---|---|---|---|
| 02-01 | NMP | 15.0% | 55.0% | 30.0% |
| 02-02 | NMP | 15.0% | 42.5% | 42.5% |

Example 13

Pharmacodynamic Analysis of Local Anesthetic Formulations in Pigs

Two formulations, 02-01 (Example 12) and 07-03 (Example 9), were evaluated for their capacity to reduce post-surgical incisional pain in a porcine model system. In this model, a 7 cm long skin and fascia incision is made in the left flank under general anesthesia. Two milliliters of test formulation was either injected into the tissue around the wound or instilled directly into the wound while the control group received saline injected around the wound (n=4 for each group). The skin incision was then closed using sterile sutures.

Post-operative pain was assessed using the Von Frey methodology. Von Frey filaments (Ugo Basile) were applied at approximately ~0.5 cm proximal to the incision line to the surface of the flank skin. Filaments were applied until the animal withdrew from the stimuli (the act of moving away from the stimuli). Each filament was applied 3-5 times. If withdrawal was not achieved, a thicker filament was applied. The maximum force filament is 60 g. If a withdrawal was achieved, a thinner filament was applied (thicker or thinner refers to thicker/higher or thinner/lower gram force). By alternating the filament thickness, the gram force required to achieve withdrawal reaction was determined and recorded.

TABLE 13-1

Anesthetic Polyorthoester-Aprotic Solvent Formulations: Reduction of Post-Surgical Incisional Pain in a Porcine Model System

| Gram Force | Baseline | 1 Hrs | 3 Hrs | 5 Hrs | Day 1 | Day 2 | Day 3 | Day 4 | Day 5 | Day 6 |
|---|---|---|---|---|---|---|---|---|---|---|
| Control Saline Injection | 60 | 1.35 | 1.7 | 2 | 1.1 | 3 | 3.35 | 4.5 | 6.5 | 6.5 |
| Sample 02-01 Instilled | 60 | 60 | 51.5 | 51.5 | 34.5 | 23.25 | 20.5 | 10.25 | 17.75 | 40.25 |
| Sample 02-01 Injected | 60 | 14.25 | 13.75 | 48.75 | 6.5 | 3 | 8 | 6.5 | 10.25 | 29 |
| Sample 07-03 Instilled | 60 | 60 | 51.5 | 60 | 40.25 | 13.75 | 11.5 | 6 | 15 | 24.5 |
| Sample 07-03 Injected | 60 | 43 | 60 | 36.25 | 22.5 | 22 | 12.75 | 6 | 11.5 | 14.25 |

Example 14

Buprenorphine Delivery Systems Comprising an Aprotic Solvent

Compositions containing between 76.2% to 62.1% polyorthoester of formula III, prepared with 0.1% of glycolic ester $R^1$, between 30.0% and 42.5% of an aprotic solvent, and between 4.9% and 15.0% buprenorphine were prepared. The composition was prepared by first the dissolving the appropriate amount of buprenorphine into the appropriate amount of aprotic solvent at approximately 80° C. The drug solution was then mixed with the appropriate amount of polymer at an elevated temperature, until homogenous. Exemplary compositions are presented in Table 13-1.

TABLE 14-1

Buprenorphine Delivery Systems:
Polyorthoester-Aprotic Solvent Compositions

| Formulation ID | Solvent ID | % Drug | % POE | % Solvent |
|---|---|---|---|---|
| 03-01 | DMSO | 7.23% | 76.08% | 18.09% |
| 03-02 | DMSO | 15.00% | 67.20% | 17.90% |
| 03-03 | NMP | 6.94% | 62.10% | 30.99% |
| 03-04 | DMSO | 4.91% | 76.22% | 18.86% |

Example 15

In-Vitro Release of Buprenorphine Compositions

The release of buprenorphine from the composition was determined by placing a small amount of the polymer formulation (approximately 25 mg) into 150 mL of phosphate buffered saline containing 0.05% cetyl trimethylammonium bromide. The samples were then incubated at 37° C. without agitation. At predetermined intervals, 1 mL samples were taken from the vials without any agitation of the solution. Each sample was analyzed by HPLC to determine the concentration of buprenorphine. The cumulative drug release from the 25 mg depot was then calculated.

TABLE 15-1

In Vitro Release of Buprenorphine

| | Percent Bupivacaine Released for Compositions | | | |
|---|---|---|---|---|
| Composition # | 1 day | 6 days | 15 days | 22 days |
| 03-01 | 18 | 35 | 55 | 81 |
| 03-02 | 16 | 44 | 80 | N/A |
| 03-03 | 5 | 80 | N/A | N/A |
| 03-04 | 5 | 73 | N/A | N/A |

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A delivery system, comprising:
   (i) a polyorthoester represented by Formula III,

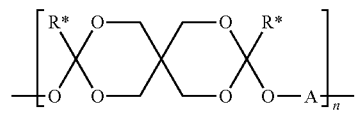

where
A is $R^1$ or $R^3$,
R* is C1-4 alkyl,
n ranges from 5 to 1000,
$R^1$ is:

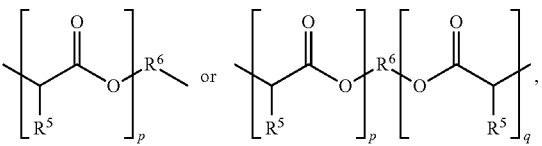

p and q are integers that vary from between about 1 to 20 and the average number of p or the average of the sum of p and q is between 1 and 7;
$R^3$ and $R^6$ are each independently:

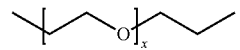

x is an integer of 0-10;
$R^5$ is H or methyl, and
the fraction of A units that are of formula $R^1$ is between 0 and 25 mole percent;
   (ii) a solvent consisting essentially of one or more aprotic solvents, wherein at least one of the one or more aprotic solvents is selected from dimethyl sulfoxide, dimethyl acetamide, and N-methyl pyrrolidone, in which the polyorthoester is miscible to form a single phase; and
   (iii) a therapeutically active agent dispersed or solubilized in the single phase.

2. The delivery system of claim 1, wherein the solvent is an organic solvent having a water solubility of greater than 25% by weight of the solvent in water at room temperature.

3. The delivery system of claim 1, wherein the solvent is a dipolar aprotic solvent having a dipole moment greater than 2 Debye.

4. The delivery system of claim 1, wherein the solvent is dimethyl sulfoxide.

5. The delivery system of claim 1, wherein the solvent is N-methyl pyrrolidone.

6. The delivery system of claim 1, wherein the therapeutically active agent is an anti-emetic, a local anesthetic or an opioid.

7. The delivery system of claim 6, wherein the therapeutically active agent is granisetron, ropivacaine, or bupivacaine.

8. The delivery system of claim 1, wherein A is $R^1$ in 0 to 10% of the monomeric units of the polyorthoester.

9. The delivery system of claim 1, wherein the active agent is granisetron in an amount between 1-5 percent by weight of the delivery system, and the solvent is DMSO in an amount between 10-35 percent by weight of the delivery system.

10. The delivery system of claim 1, wherein the system is flowable, and the solvent has a dipole moment greater than 2 Debye (D).

11. The delivery system of claim 10, wherein the therapeutically active agent is an anti-emetic, a local anesthetic or an opioid.

12. The delivery system of claim 11, wherein the therapeutically active agent is granisetron, ropivacaine, or bupivacaine.

13. The delivery system of claim 10, wherein A is $R^1$ in 0 to 10% of the monomeric units of the polyorthoester.

14. The delivery system of claim 10, wherein the active agent is granisetron in an amount between 1-5 percent by weight of the composition, and the solvent is DMSO in an amount between 10-35 percent by weight of the composition.

15. The delivery system of claim 1, wherein $R^3$ and $R^6$ are both —(CH$_2$—CH$_2$—O)$_2$—(CH$_2$—CH$_2$)—; $R^5$ is hydrogen; and p is 1 or 2.

16. The delivery system of claim 1, wherein the polyorthoester comprises subunits selected from

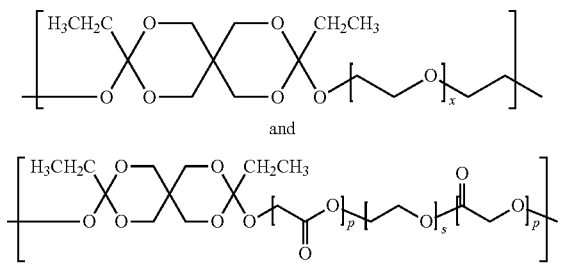

and where
x is an integer from 1-4,
the total amount of p is an integer from 1-20, and
s is an integer from 1-4.

17. The delivery system of claim 1, wherein the polyorthoester comprises alternating residues of 3,9-diethyl-3,9-2,4,8,10-tetraoxaspiro[5.5]undecane-3,9-diyl,

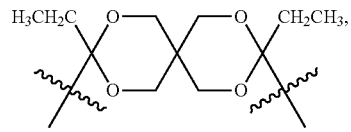

and a diol-ate residue of triethylene glycol or of triethylene glycol diglycolide, and comprises from about 0 to about 25 mole percent of glycolide-containing subunits.

18. The delivery system of claim 17, wherein the polyorthoester has a molecular weight of 1,000 Da to 10,000 Da.

19. The delivery system of claim 1, wherein the polyorthoester is prepared by reacting diketene acetal, 3,9-di(ethylidene)-2,4,8,10-tetraoxaspiro[5.5]undecane,

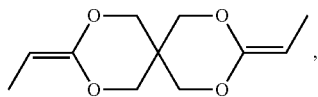

with triethylene glycol and triethylene glycol diglycolide.

20. The delivery system of claim 19, wherein the polyorthoester comprises about 20 mole percent $R^1$, where $R^1$ is triethylene glycol diglycolide, and 80 mole percent $R^3$, where $R^3$ is triethylene glycol.

21. The delivery system of claim 1, wherein the aprotic solvent is dimethyl acetamide.

* * * * *